United States Patent
Peti-Peterdi

(10) Patent No.: US 10,828,374 B2
(45) Date of Patent: Nov. 10, 2020

(54) TARGETING MACULA DENSA CELLS AS A NEW THERAPEUTIC APPROACH FOR KIDNEY DISEASE

(71) Applicant: MACULA DENSA CELL LLC, Palos Verdes Estates, CA (US)

(72) Inventor: Janos Peti-Peterdi, Los Angeles, CA (US)

(73) Assignee: MACULA DENSA CELL LLC, Palos Verdes Estates, CA (US)

( * ) Notice: Subject to any disclaimer, the term of this patent is extended or adjusted under 35 U.S.C. 154(b) by 0 days.

(21) Appl. No.: 15/806,221

(22) Filed: Nov. 7, 2017

(65) Prior Publication Data
US 2018/0133336 A1    May 17, 2018

Related U.S. Application Data

(60) Provisional application No. 62/418,691, filed on Nov. 7, 2016.

(51) Int. Cl.
| | |
|---|---|
| *A61K 38/00* | (2006.01) |
| *A61K 47/64* | (2017.01) |
| *C12N 15/113* | (2010.01) |
| *A61P 13/12* | (2006.01) |
| *C07K 14/47* | (2006.01) |
| *C07K 14/475* | (2006.01) |
| *A61K 49/00* | (2006.01) |

(52) U.S. Cl.
CPC .......... *A61K 47/64* (2017.08); *A61K 47/6455* (2017.08); *A61K 49/0008* (2013.01); *A61P 13/12* (2018.01); *C07K 14/47* (2013.01); *C07K 14/475* (2013.01); *C12N 15/113* (2013.01); *C12N 2310/141* (2013.01); *C12N 2310/3513* (2013.01); *C12N 2320/32* (2013.01)

(58) Field of Classification Search
None
See application file for complete search history.

(56) References Cited

U.S. PATENT DOCUMENTS

2008/0214653 A1*  9/2008  Zicker .................. A61K 31/205
                                                                        514/440

OTHER PUBLICATIONS

Yang et al. The Journal of Biological Chemistry, vol. 275, No. 48, Issue of Dec. 1, pp. 37922-37929, 2000.*
Harris, Raymond, European Renal Association, Nephrology Dialysis Transplantation, 2000.*
Peti-Peterdi et al.: Macula Densa Sensing and Signaling Mechanisms of Renin Release. J Am Soc Nephrol. 21(7):1093-1096 (2010).
Peti-Peterdi: Newly STEMming functions of macula densa-derived prostanoids. Hypertension. 65(5):987-988 (2015).
Yang et al.: Salt Restriction Leads to Activation of Adult Renal MSC-Like Cells via PGE2 and EP4 Receptor. Hypertension. 65(5):1047-1054 (2015).

* cited by examiner

*Primary Examiner* — Jeanette M Lieb
(74) *Attorney, Agent, or Firm* — Wilson Sonsini Goodrich & Rosati

(57) ABSTRACT

There is no specific cure for chronic kidney disease (CKD), which affects one in every ten adults. The unmet medical need has created significant interest in regenerative therapeutic approaches. Described herein is a radically new and innovative therapeutic approach identified by characterizing a novel mechanism of renal tissue repair and its role in glomerular injury. By targeting this mechanism in CKD, significant therapeutic benefit supported by rapid cellular remodeling of kidney tissues, coincident with structural and functional nephron regeneration. Methods and compositions for achieving the described therapeutic approach are fundamentally different from existing strategies.

12 Claims, 25 Drawing Sheets

Specification includes a Sequence Listing.

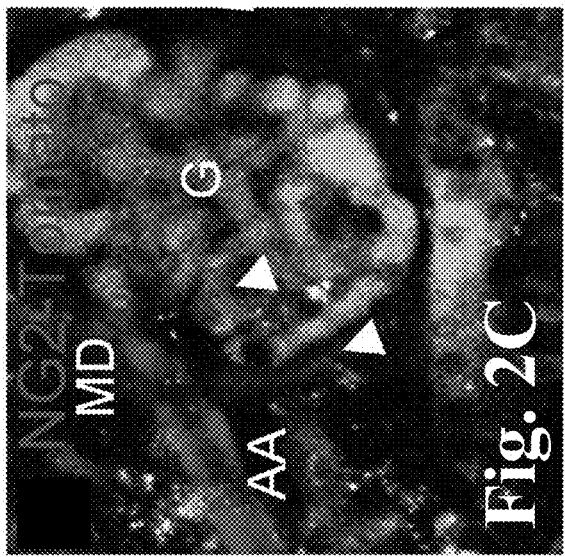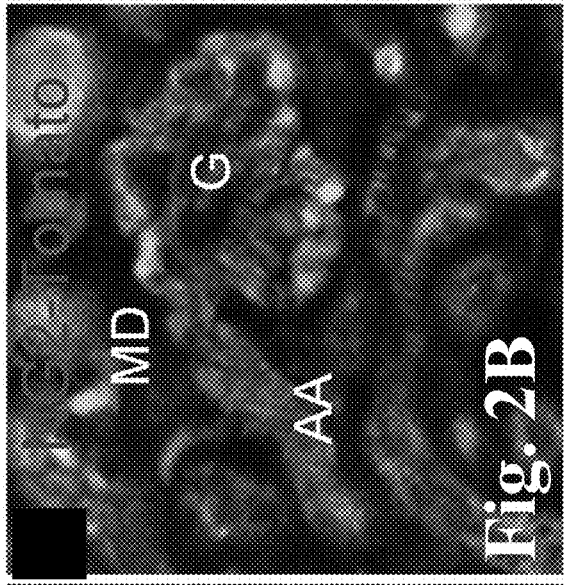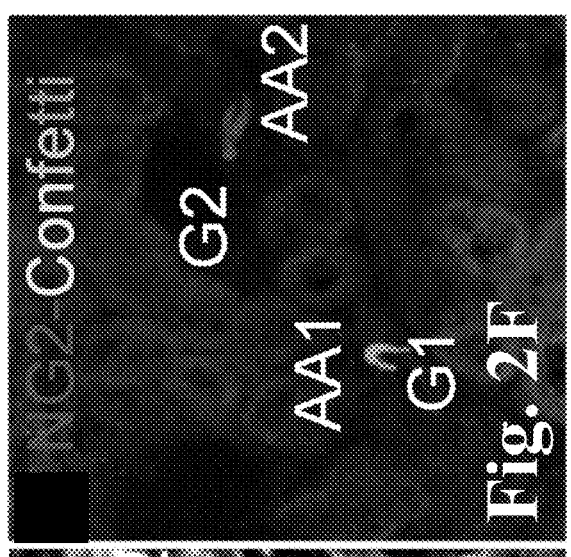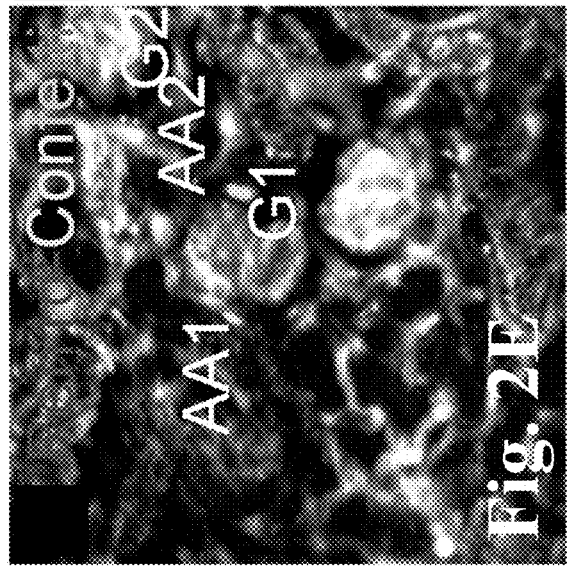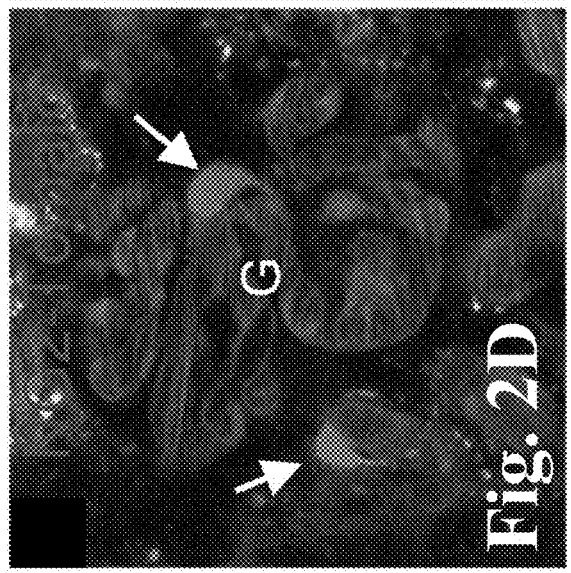

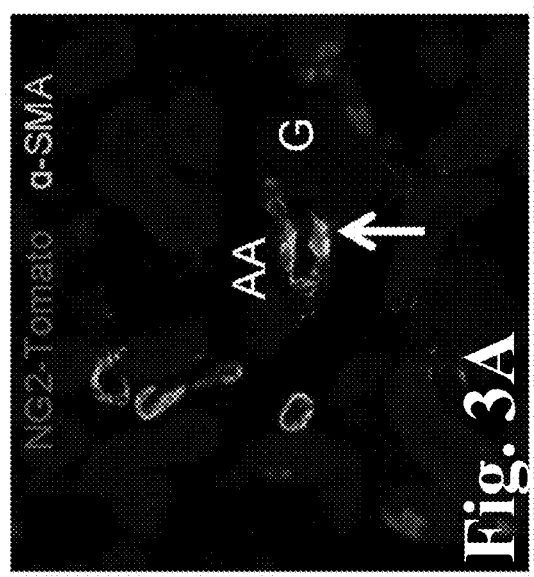
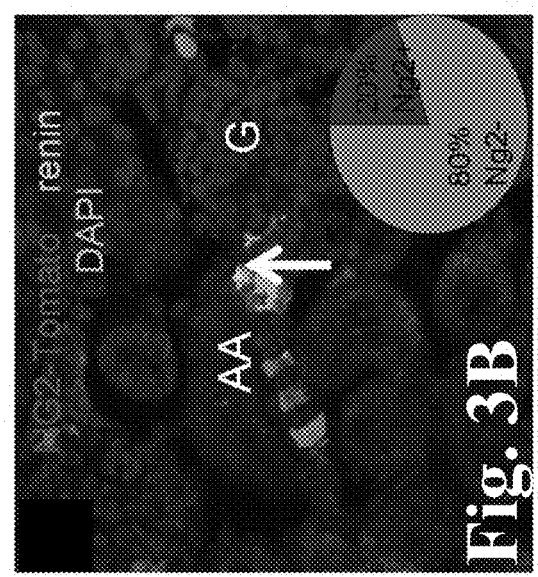
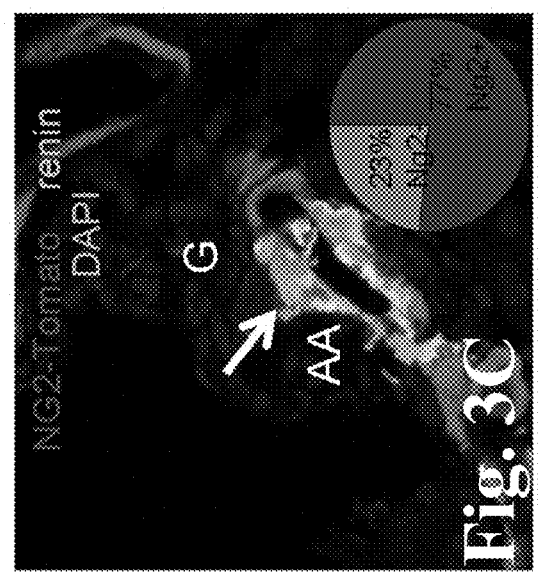
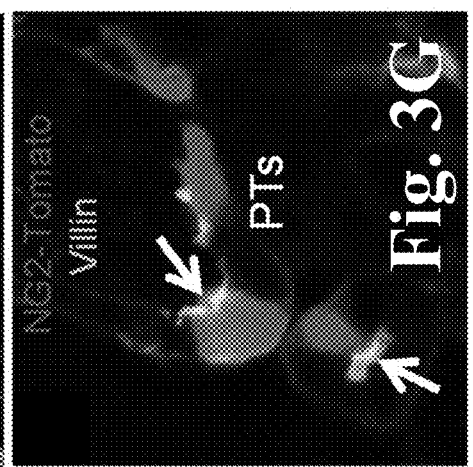
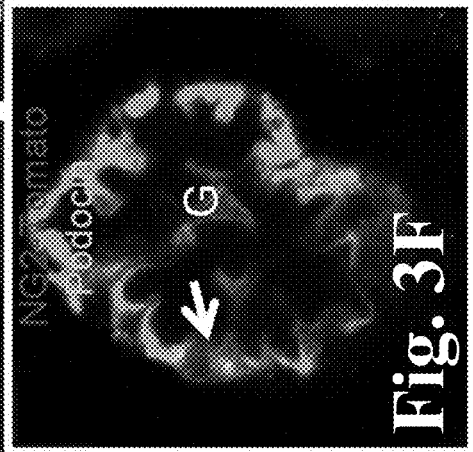
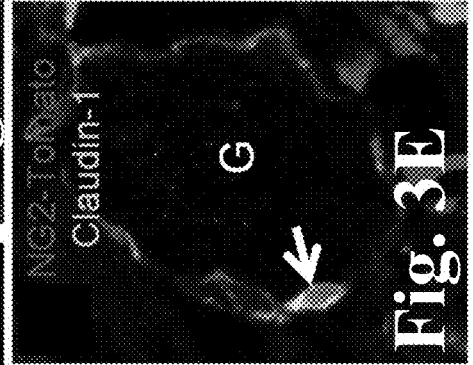
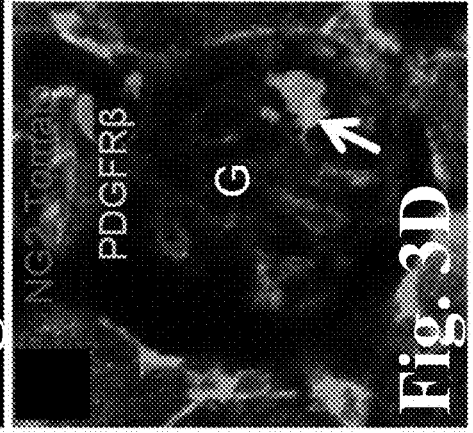

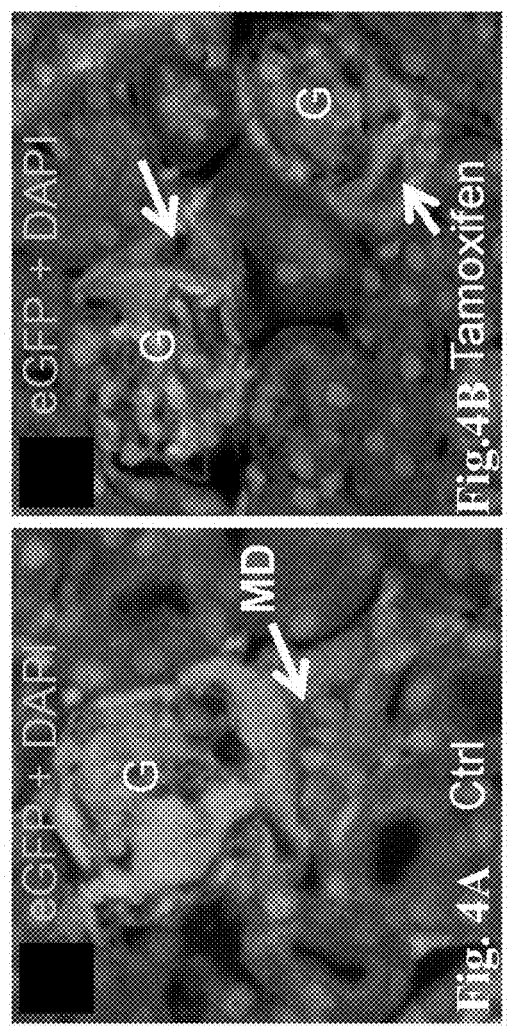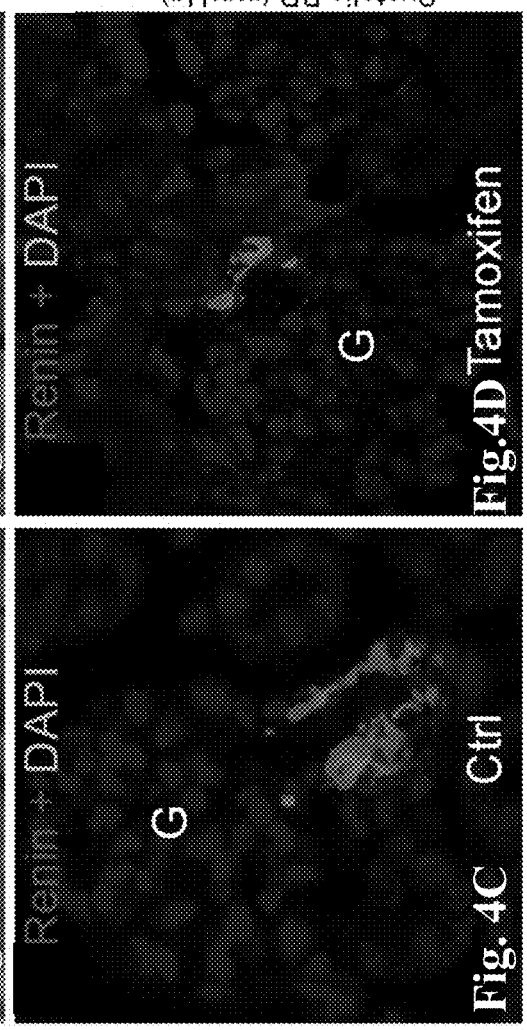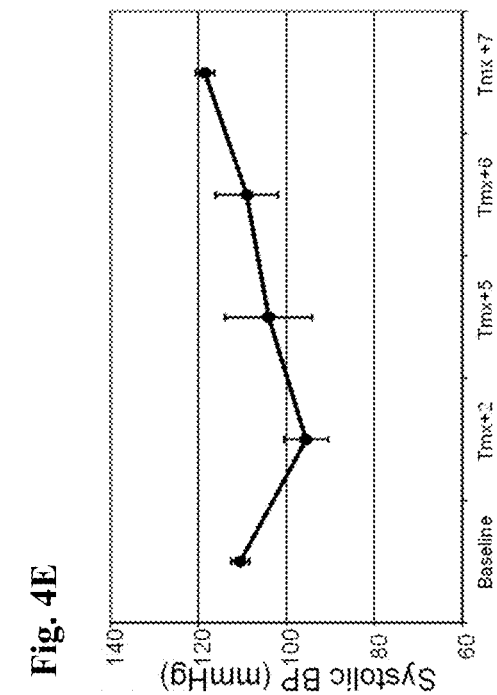

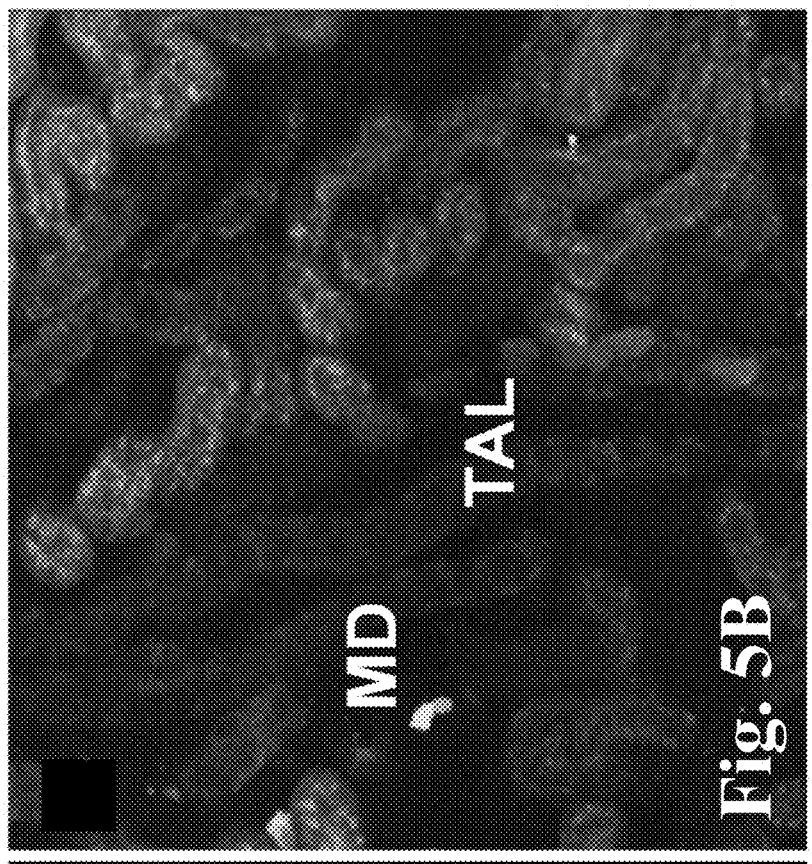
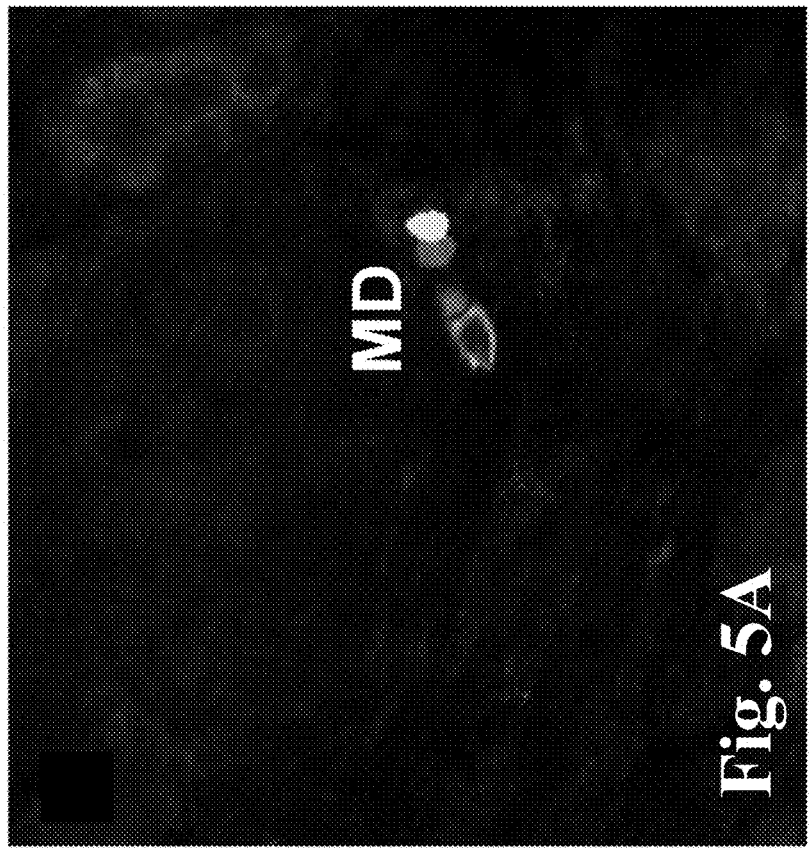

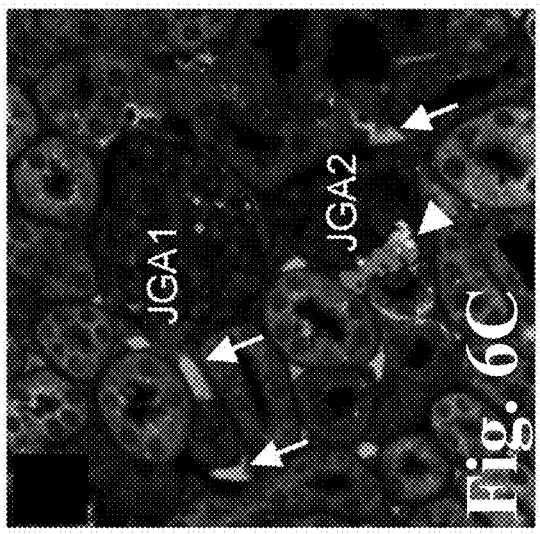
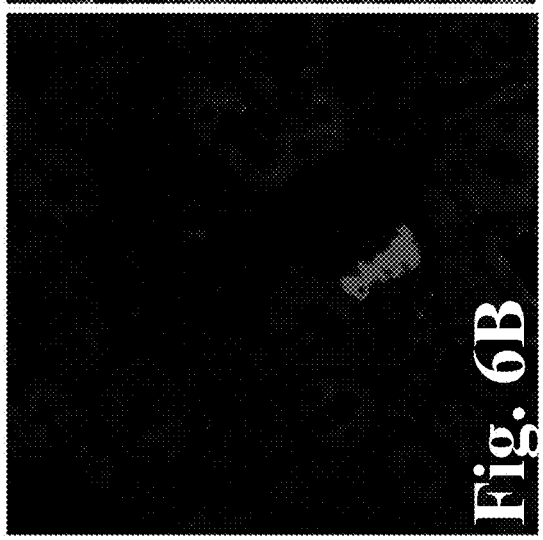
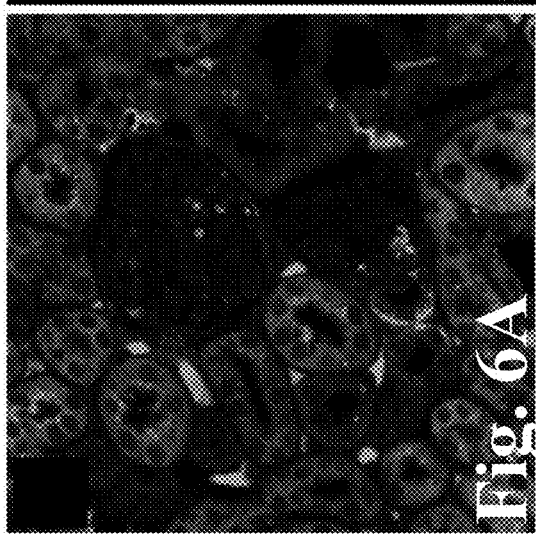
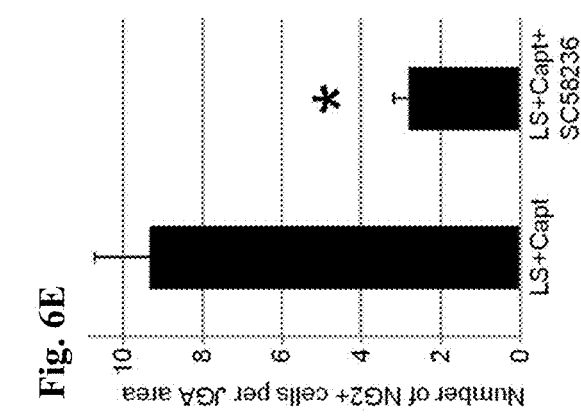
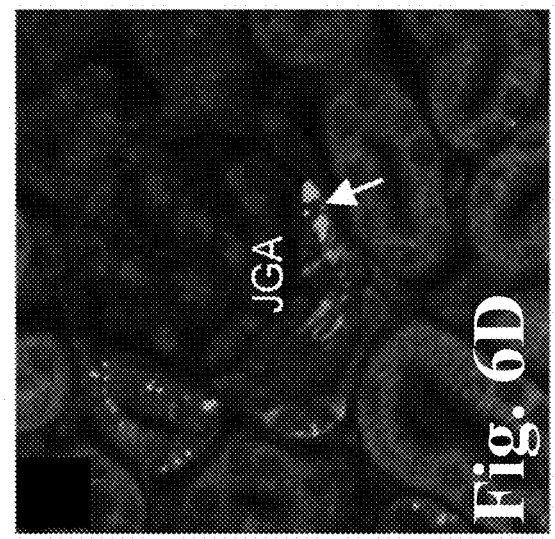

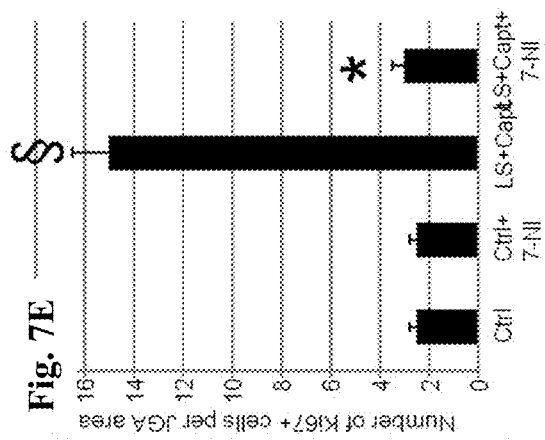
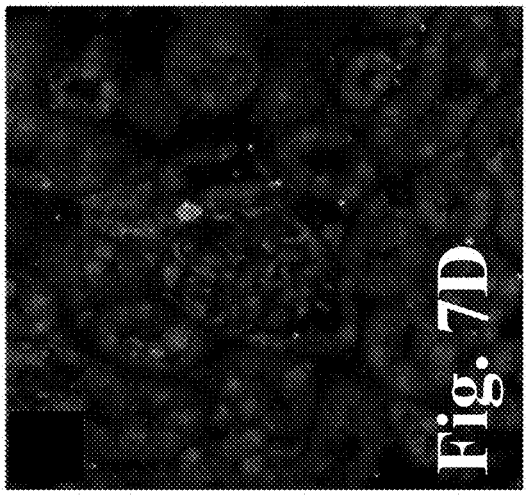

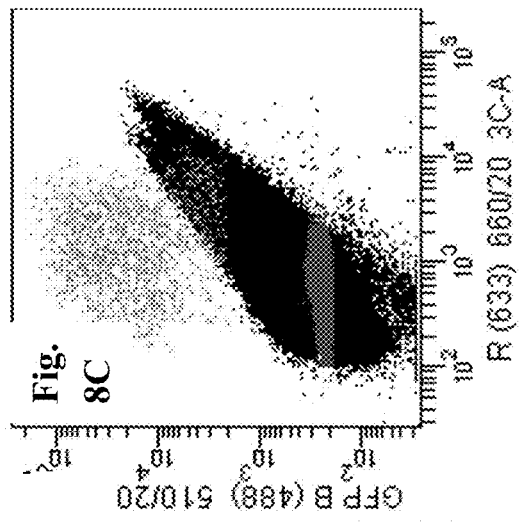
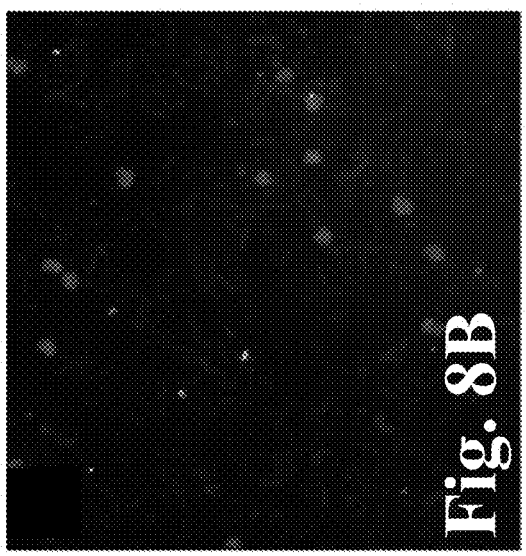
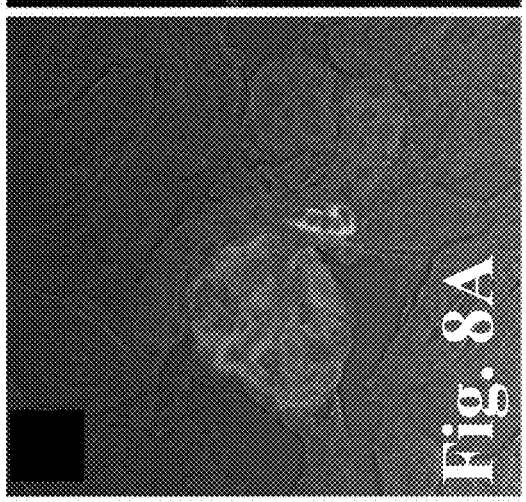
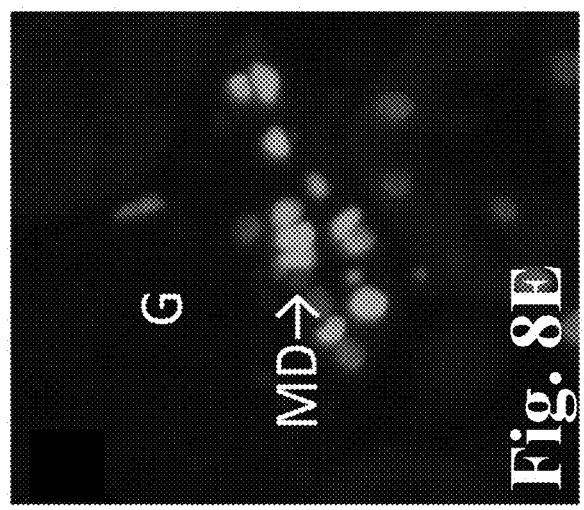
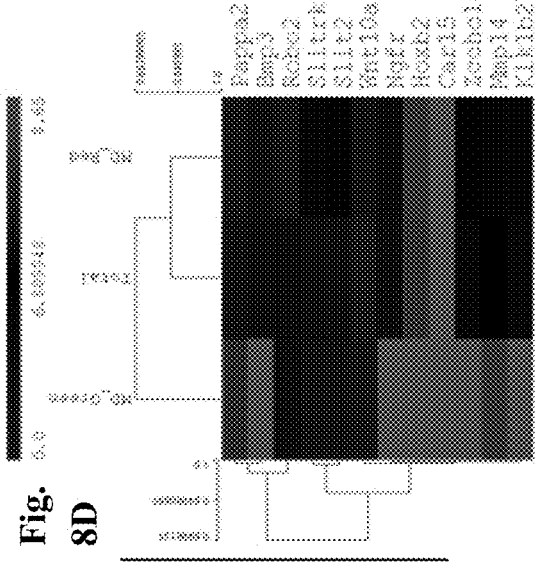

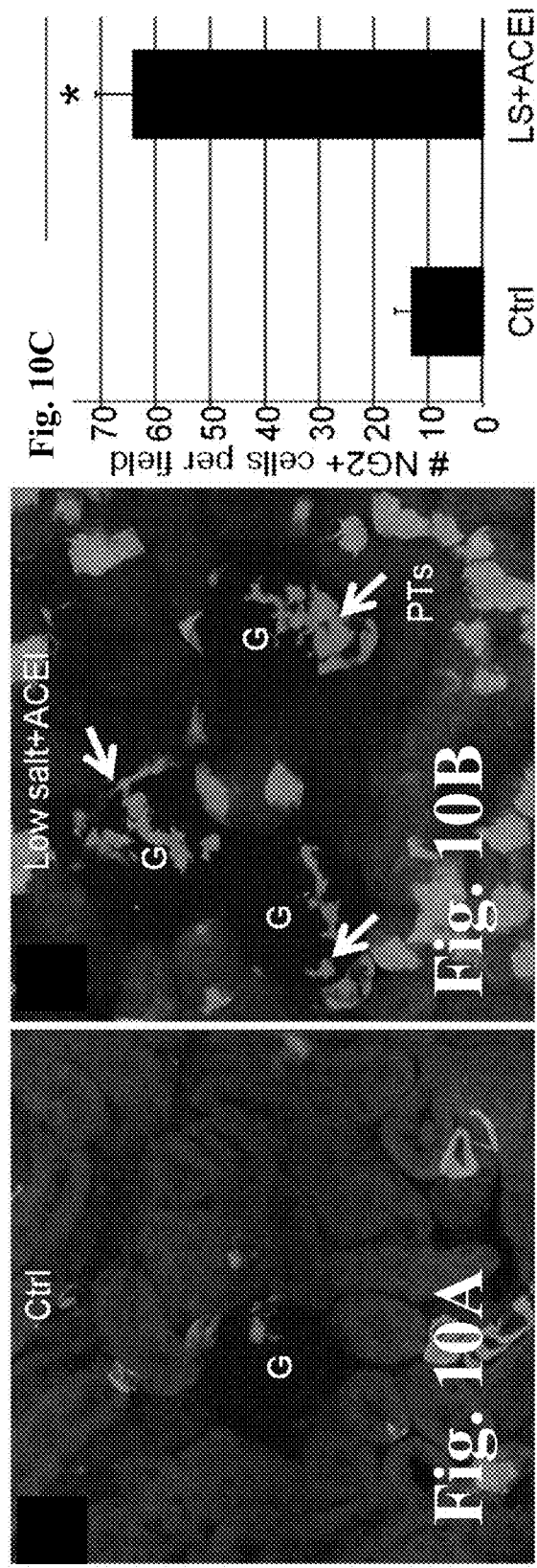

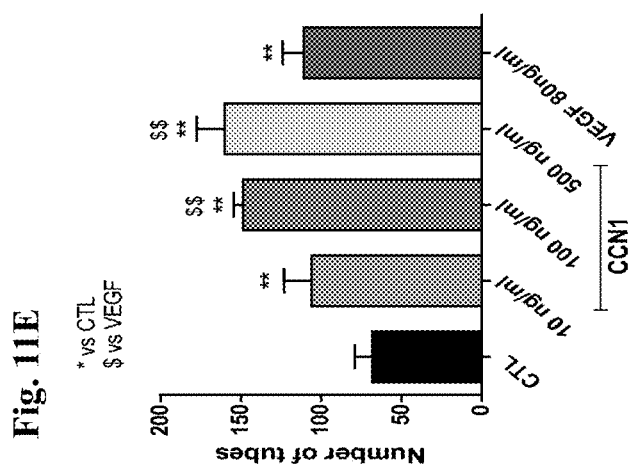
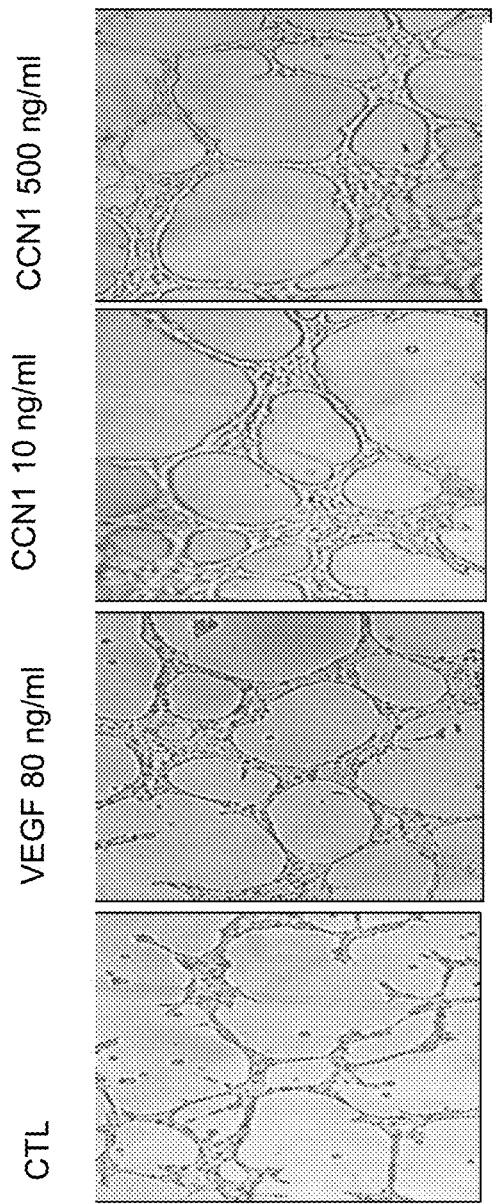

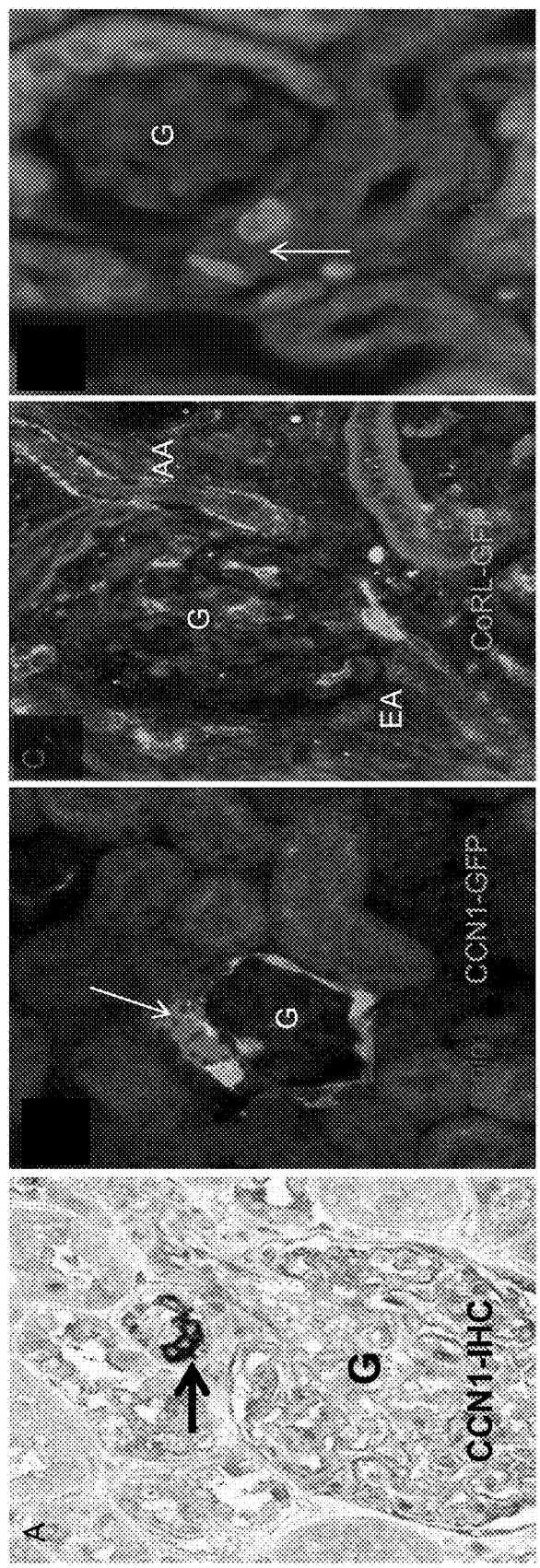

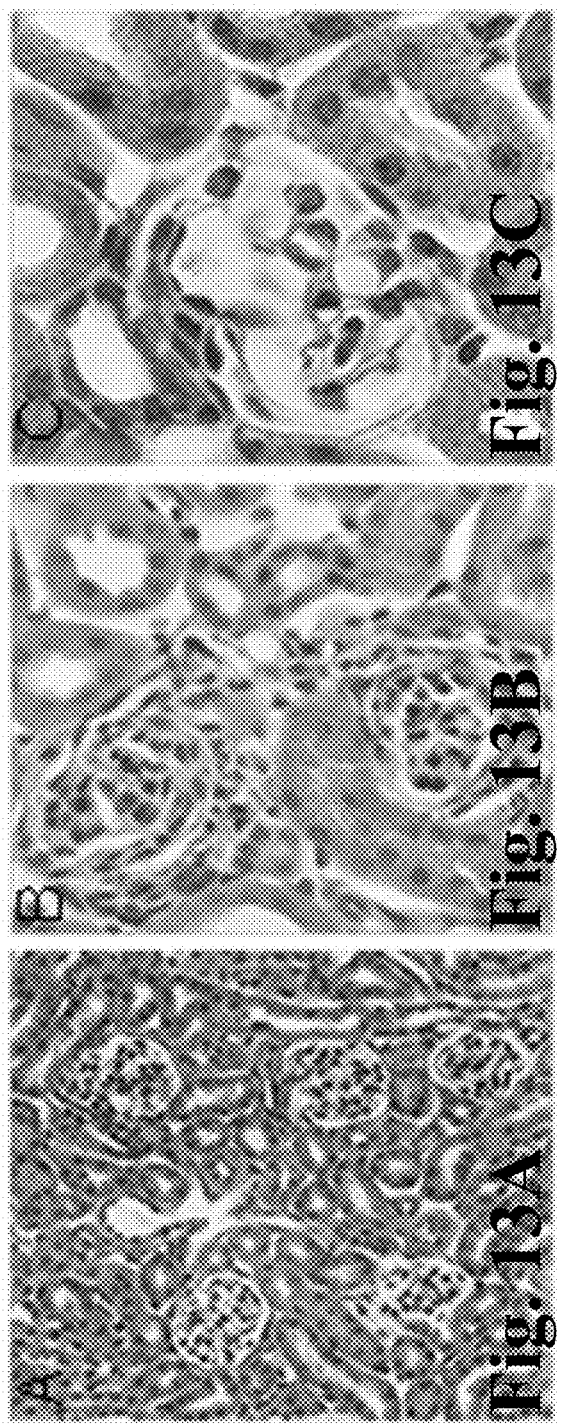
Fig. 13A  Fig. 13B  Fig. 13C
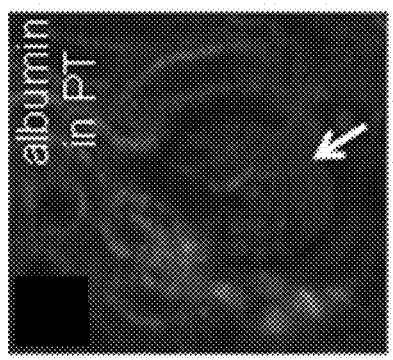
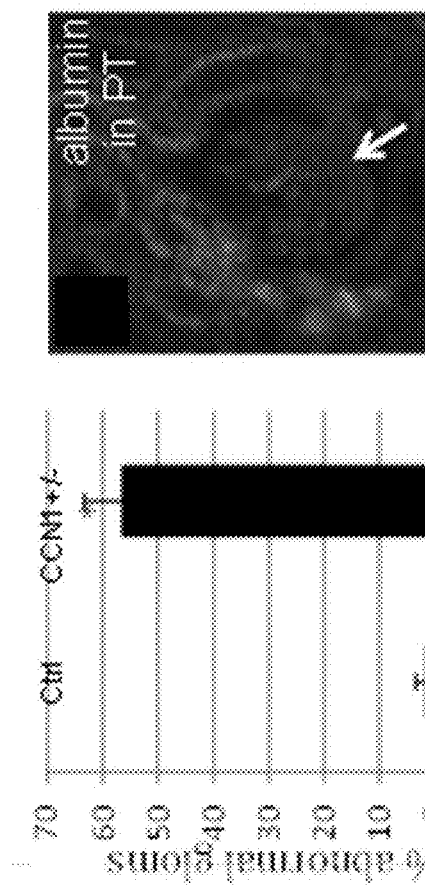
Fig. 13D  Fig. 13E

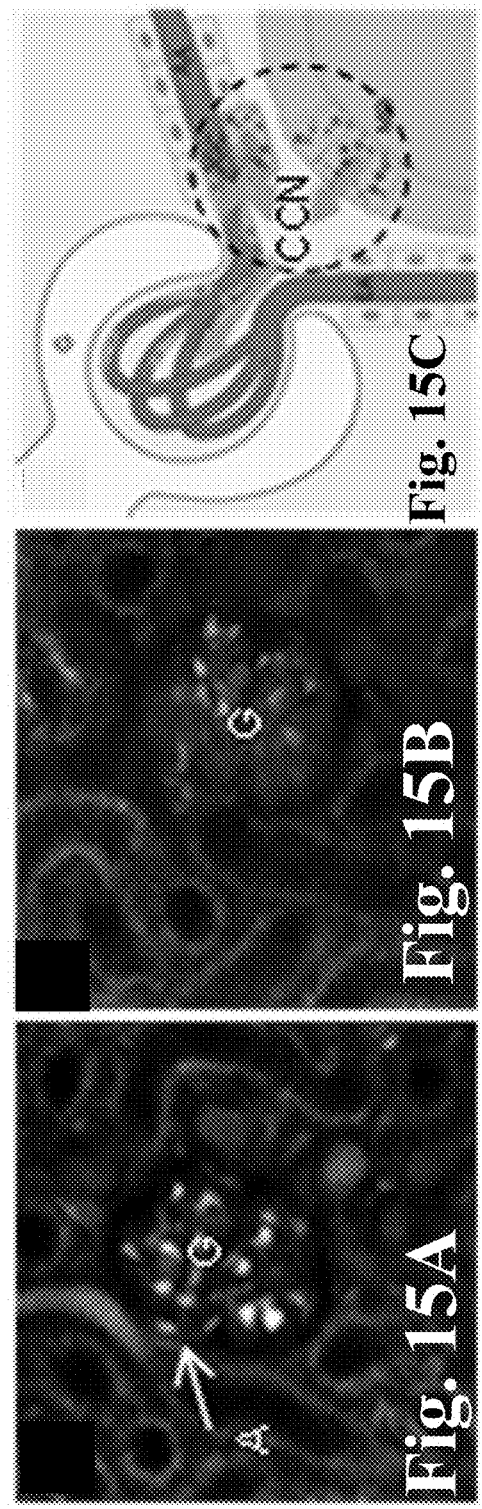
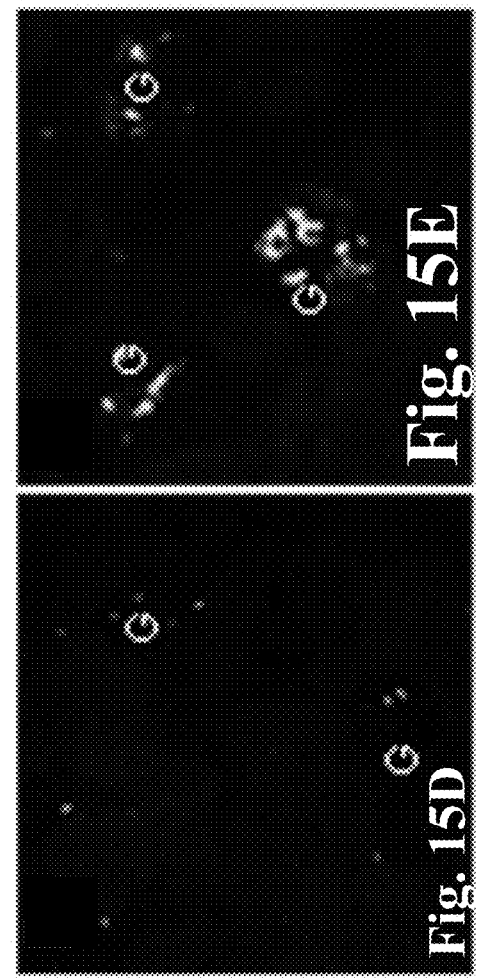

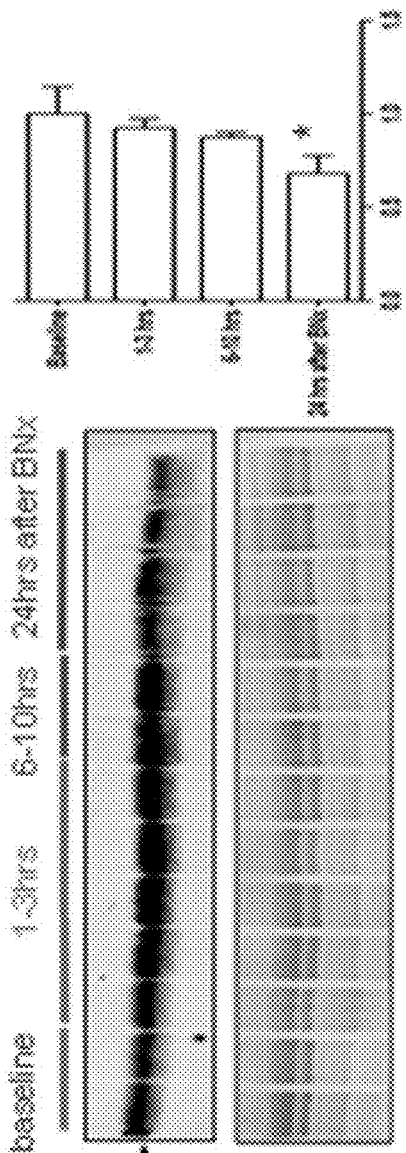
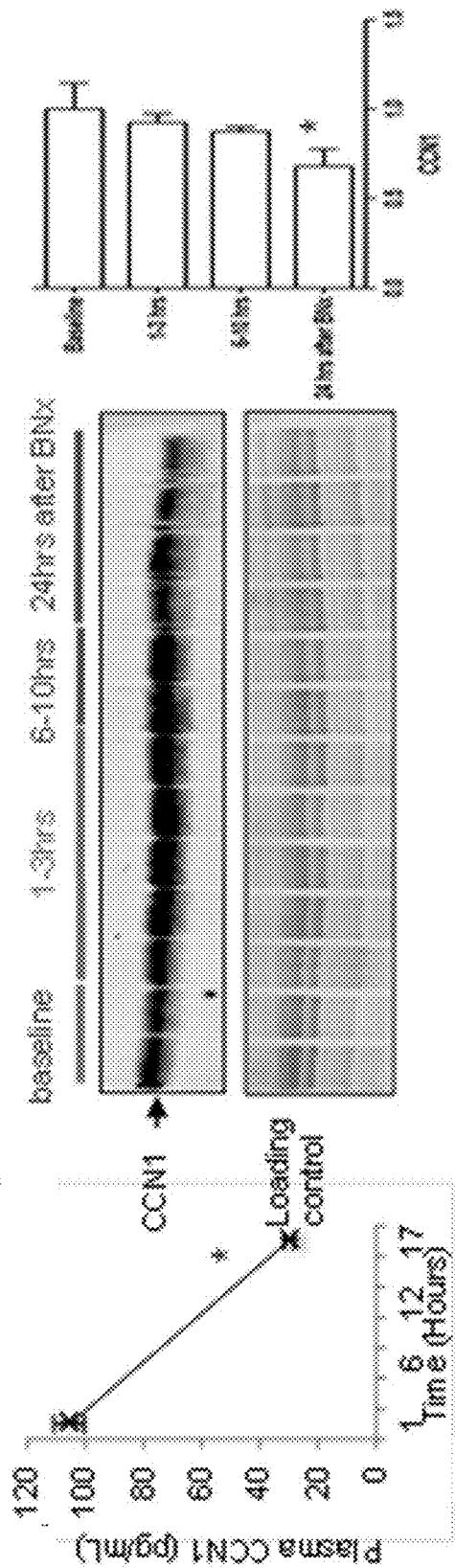
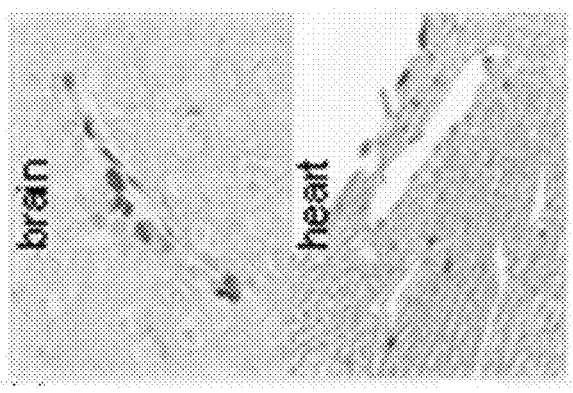
Fig. 16A
Fig. 16B
Fig. 16C

SEQUENCE LISTING

```
<160> NUMBER OF SEQ ID NOS: 1

<210> SEQ ID NO 1
<211> LENGTH: 42
<212> TYPE: PRT
<213> ORGANISM: Artificial Sequence
<220> FEATURE:
<223> OTHER INFORMATION: homing peptide

<400> SEQUENCE: 1

Ala Cys Phe Asn Asp Ser Asp Met Leu Cys Gly Gly Gly Lys Lys His
1               5                   10                  15

Leu Leu Ala His Ala Leu His Leu Leu Ala Leu Leu Ala Leu His Leu
            20                  25                  30

Ala His Ala Leu Ala His Leu Lys Lys Ala
        35                  40
```

TARGETING MACULA DENSA CELLS AS A NEW THERAPEUTIC APPROACH FOR KIDNEY DISEASE

CROSS-REFERENCE TO RELATED APPLICATIONS

This application claims the benefit of priority under 35 U.S.C. § 119(e) to U.S. provisional patent application No. 62/418,691 filed Nov. 7, 2016, the entirety of which is hereby incorporated by reference.

STATEMENT REGARDING FEDERALLY SPONSORED RESEARCH OR DEVELOPMENT

This invention was made with government support under Grant No. DK064324 awarded by National Institutes of Health. The government has certain rights in the invention.

FIELD OF INVENTION

Described herein are novel therapeutic approaches in kidney disease, targeting macula densa cells.

BACKGROUND

Glomerular dysfunction is a common basis for the development of chronic kidney disease (CKD), a condition with significant comorbidities and mortalities. There are about 20 million people in the US who suffer from chronic kidney disease (CKD). Diseases of the glomerulus account for 75% of CKD cases. The loss of normal kidney function requires high-cost renal replacement therapies (dialysis, transplantation) and is associated with even higher morbidity and mortality. Currently there is no cure for CKD other than non-specific drugs that only slow down progression to end-stage. The unmet medical need and inadequacy of current treatments have led to great interest in regenerative therapeutic approaches for CKD. Nephrons display some level of repair capability. Acute damage to nephrons can be repaired, mostly by proliferation of local renal cells rather than by circulating multipotent cells.

However, nephrogenesis ceases shortly after birth, so severely damaged nephrons are never replaced. Several studies showed that the injection of stem cells of various origin into a mouse model of acute kidney injury greatly improved renal function and survival of the animals, and the stem cells were seen to be integrated into tubules, glomeruli, and peritubular areas. None of these studies, however, have demonstrated de novo nephron formation or significant glomerular/nephron remodeling. It is this ability which must be the Inventors' goal to reverse end-stage renal disease. It is possible that nephron generation through stem cell therapy may require a more targeted approach, such as through the identification of cells that function both as progenitors as well as organizers of nephron architecture. Thus, there is a great need in the art for approaches that can support de novo nephron formation or significant glomerular/nephron remodeling.

The Inventors believe macula densa (MD) cells, which are strategically localized at the glomerular entrance, are one of these important cell types. MD cells are one of the mysterious, but chief cell types within the kidney, which play key sensory and regulatory functions in the maintenance of body fluid and electrolyte homeostasis and blood pressure. The metabolism and salt-sensing MD cells of the distal tubule are strategically positioned at the entrance of the glomerulus.

Preliminary work using serial intravital multiphoton microscopy (MPM) of the same intact kidney region over several days provided visual clues that, in response to MD-derived signals, progenitor cells residing in the renal interstitium proliferate and migrate towards the MD along the afferent arteriole, and via the vascular pole, into the glomerulus and tubules. This phenomenon appears to be highly augmented in MD stimulating conditions. This observation led to the indication that MD cells are angiogenic, glomerulotrophic master inducers and regulators of interstitial, vascular, and glomerular/nephron remodeling in the adult kidney. MD cells may perform this new, non-traditional function via the generation of novel secreted chemotactic, angiogenic, and trophic factors which exert their paracrine actions on the reactivation and vascular/glomerular recruitment of mesenchymal progenitor cells.

Described herein are methods and composition for activating and augmenting these novel MD mechanisms in CKD to support rapid cellular remodeling of kidney tissue, leading to structural and functional nephron regeneration. The Inventors' research has used comprehensive experimental approaches including new transgenic mouse models with fluorescently tagged cell lineages, cell fate tracking, MD gene profiling, bioinformatics, and in vivo serial MPM of the intact kidney, thereby providing new therapeutic avenues.

SUMMARY OF THE INVENTION

Described herein is composition including a peptide and a nucleic acid. In other embodiments, the peptide includes a homing peptide. In other embodiments, the peptide includes a histidine-rich amphiphatic peptide. In other embodiments, the homing peptide is capable of specifically binding to macula densa (MD) cells. In other embodiments, the nucleic acid is bound to the peptide. In other embodiments, the nucleic acid is a microRNA. In other embodiments, the microRNA includes miR-30 and/or miR-541. In other embodiments, the peptide includes the amino acid sequence SEQ ID NO:1. Further described herein is a pharmaceutical composition including the aforementioned composition and a pharmaceutically acceptable carrier.

Also described herein is a method of treating a kidney disease and/or condition including administering to a subject, a pharmaceutical composition including a peptide, a nucleic acid, and a pharmaceutically acceptable carrier. In other embodiments, the kidney disease includes chronic kidney disease. In other embodiments, the peptide is a fusiogenic peptide including a homing peptide and a histidine-rich amphiphatic peptide. In other embodiments, the fusiogenic peptide includes the amino acid sequence SEQ ID NO:1. In other embodiments, the nucleic acid is a microRNA. In other embodiments, the microRNA includes miR-30 and/or miR-541.

Further described herein is a composition including a recombinant CCN family member 1 (CCN1) peptide. In other embodiments, the recombinant CCN1 peptide includes a homing peptide.

Also described herein is a method of treatment including administration of a composition including a recombinant CCN1 peptide.

Further described herein is a composition including media conditioned by macula densa (md) cells. Also described herein is a method of treatment including administration of a composition including media conditioned by macula densa cells.

Also described herein is a method of treating a kidney disease and/or condition including administering to a subject, a therapeutically effective dose of a loop diuretic. In other embodiments, the loop diuretic includes furosemide, analogs and derivatives thereof. In other embodiments, the therapeutically effective dose activates macula densa (md) cellular repair.

BRIEF DESCRIPTION OF FIGURES

FIG. 2. In vivo MPM imaging of newly developed transgenic mouse models. FIG. 2A, FIG. 2B, FIG. 2C, FIG. 2D: Constitutive NG2-DsRed or tamoxifen-inducible NG2CreER-Tomato mice in which NG2+ mesenchymal progenitor cells (red) can be tracked. Plasma was labeled green with 500 kD dextran-Alexa488. Compared to baseline (FIG. 2A), serial MPM imaging of the kidney one (FIG. 2B) and two weeks after low salt+captopril treatment (FIG. 2C) showed increased density of cells that belong to the NG2 lineage along the afferent arteriole (AA) towards the MD (FIG. 2B) and later within the glomerulus (FIG. 2C, arrows), including parietal epithelial cells (FIG. 2C) and podocytes (FIG. 2D). FIG. 2E: Ren1d-Confetti mice in which the Ren1d lineage is labeled with the Confetti reporter construct (CFP/GFP/YFP/RFP). Cells of the AA and glomerulus (G) labeled positive. FIG. 2F: NG2 cell lineage tracing on fixed kidney sections from NG2CreER-Confetti mice treated with low salt+ACEI for one week. Several glomerular (G) afferent arterioles (AA) were labeled by monochromatic (yellow or red) multi-cell tracing units, indicating NG2 cell clonality (single progenitor cell derived).

FIG. 3. Tracking the final fate of mesenchymal progenitor (NG2+) cells in the kidney. Co-localization of endogenous NG2-Tomato fluorescence (red) with immunofluorescence of cell differentiation markers (green) for vascular smooth muscle cells (αSMA, FIG. 3A), JG renin cells (renin, FIG. 3B-FIG. 3C), mesangial cells (PDGFRβ, FIG. 3D), parietal epithelial cells (claudin-1, FIG. 3E), podocytes (podocin, FIG. 3F), and proximal tubule cells (villin, FIG. 3G). Compared to control (FIG. 3B), the percentage of NG2-derived renin cells (insets) increased significantly in response to MD cell stimulation by low salt+ACEI treatment for one week (FIG. 3C).

FIG. 4. Inducible, in vivo genetic ablation of MD cells by Cre-mediated expression of diphtheria toxin fragment A (DTA). FIG. 4A: In non-induced MD-DTA mice, eGFP fluorescence is visible in all renal cell types (strongest in glomeruli (G), mesangium, and arterioles) including the intact macula densa (arrow, MD). FIG. 4B: One week after tamoxifen induction in adult MD-DTA mice, dark, eGFP-negative MD regions are observed with no nuclear labeling (DAPI), indicating successful MD cell ablation. Compared to non-induced MD-DTA mice (FIG. 4C), the number of renin cells decreased one week after tamoxifen induction (FIG. 4D) based on renin immunofluorescence (red). FIG. 4E: MD-DTA mice were viable, appeared normal, and were able to maintain blood pressure during the first week after tamoxifen.

FIG. 5. Representative multi-color images of MD cells from a new MD-Confetti mouse model induced in adult (FIG. 5A) or on day 1 after birth (P1) (FIG. 5B). FIG. 5A: MD-Confetti mice with tamoxifen-inducible expression of the confetti fluorescent reporter construct (membrane CFP/nuclear GFP/cytosolic YFP/RFP) feature MD cells labeled in all four colors. FIG. 5B: In vivo lineage tracing shows exclusively clonal (i.e. single-color, red) multi-cell tracing units in TALs originated from a single red MD progenitor cell. Image shows kidney of 3 weeks old mouse induced by single tamoxifen injection at P1.

FIG. 6. NG2 (FIG. 6A, green) and renin (FIG. 6B, red) immunofluorescence of low salt diet+captopril-treated mouse kidneys. Overlay (FIG. 6C) shows the high density of NG2+ cells around the JGA (arrows) and that some NG2+ cells express renin (arrowhead). Selective COX-2 inhibition with SC58236 significantly reduced the number of NG2+ cells in the JGA area (FIG. 6D-FIG. 6E). Nuclei were labeled blue with DAPI. n=4 each group, *: P<0.05.

FIG. 7. Ki67 (red nuclei) immunofluorescence of control (FIG. 7A-FIG. 7B) and low salt diet+captopril-treated mouse kidneys (FIG. 7C-FIG. 7D). In contrast to control untreated (FIG. 7A) and control+7-NI (FIG. 7B), a high density of Ki67+ proliferating cells are visible around the JGA interstitium in response to low salt diet+captopril treatment (FIG. 7C). The selective nNOS inhibitor 7-NI significantly reduced the number of Ki67+ cells in the JGA area (FIG. 7D-FIG. 7E). Nuclei were labeled blue with DAPI. n=4 each group, §: P<0.05 versus ctrl, *: P<0.05 versus untreated low salt+captopril.

FIG. 8. Illustration of the Inventors' MD cell isolation and bioinformatics approach. High-efficiency MD cell harvest was performed from freshly digested MD-GFP mouse kidneys followed by MD cell isolation with fluorescence-activated cell sorting (FACS). FIG. 8A: MD-GFP mice feature MD-specific GFP expression while all other cell types in the renal cortex (most intensely the glomeruli and distal nephron-collecting ducts) are labeled with Tomato (red). FIG. 8B: Rapid tissue digestion resulted in the appearance of isolated MD cell plaques (intense green objects surrounded by red or non-labeled cells and structures). FIG. 8C: GFP+, Tomato+, and non-labeled cells were separated by FACS. FIG. 8D: Heat map of some of the top enriched MD genes illustrate their MD-specificity compared to whole kidney and Tomato+ cell profiles. FIG. 8E: Kidney section from TCF/Lef:H2B-GFP Wnt/β-catenin reporter mice identify that MD cells are one renal cell type with the highest Wnt/β-catenin signaling activity (courtesy of Dr. Jeremy Duffield). This is consistent with their high Wnt10a expression (FIG. 8D).

FIG. 10: Robust increase in renal cortical NG2+ cell density in response to low salt+ACEI diet. NG2+ cell fate mapping on histological sections in NG2CreER-Tomato mice (8 weeks of age, 3 weeks after tamoxifen induction)

identified a significantly increased (5-fold) density of NG2+ cells in the renal cortex after low salt+ACEI treatment for one week (FIG. 10B) compared to untreated controls (FIG. 10A). Highest NG2+ cell density was observed in (juxta) glomerular areas (arrows). Green shows tissue autofluorescence for visualizing morphology. FIG. 10C: Values are mean±SE. *p<0.05 vs control.

FIG. 11. Robust effect of CCN1 on GEnCs: in vitro angiogenesis. Endothelial tube formation assays were performed using cultured GEnCs and standard doses of CCN1 and VEGF. *: P<0.05. Results are shown in FIG. 11A, FIG. 11B, FIG. 11C, FIG. 11D and FIG. 11E.

FIG. 12. Robust and constitutive expression of CCN1 in the JGA in the human (FIG. 12A) and mouse kidney (FIG. 12B, FIG. 12C, FIG. 12D). FIG. 12A: CCN1 expression in MD cells (arrow) was confirmed on the protein level using data from the Human Protein Atlas. FIG. 12B: In transgenic mice in which GFP expression was driven by CCN1 promoter activity, GFP was localized to the JGA including both MD cells and cells of the renin lineage (CoRL) (JG and VSMC cells, mesangium, PECs). Co-localization of genetic GFP signal with renin immunofluorescence (red) identified CCN1 expression in actively renin-secreting cells. FIG. 12C: In Ren1d-mTmG mice, CoRL is labeled green (identical to FIG. 12B). FIG. 12D: CCN1 immunofluorescence labeled JG renin and MD cells (red).

FIG. 13. Structural and functional consequences of JGA-specific CCN1 knockout in the mouse kidney. FIG. 13A, FIG. 13B, FIG. 13C: H&E staining of control (FIG. 13A) and heterozygous Ren1d-Cre/CCN1fl mice (FIG. 13B-FIG. 13C) showing severe mesangial expansion (FIG. 13B) and a few dilated capillaries (FIG. 13C). FIG. 13D: Analysis of the number of abnormal glomeruli showing >50% glomeruli were affected in CCN1 KO mice. FIG. 13E: Intravital MPM imaging of heterozygous Ren1d-Cre/CCN1fl mice revealed high albumin leakage (red) from aberrant glomerular capillaries. Arrow points to high albumin containing Bowman's space. Albumin uptake in proximal tubules (PT) is also high, indicating high glomerular permeability to albumin.

FIG. 15. Tracking the fate of the same glomerular endothelial cells over time in vivo at the single cell level. FIG. 15A-FIG. 15B: Serial MPM imaging of the same glomerulus (G) in the same Cdh5-Confetti mice was performed daily for one week. Endothelial cell distribution was registered using Z-sectioning of the glomerulus from top to bottom at each time point. Compared to baseline (FIG. 15A) when cells of all Confetti colors (membrane-bound CFP (blue), nuclear GFP (green), cytosolic YFP (yellow) and RFP (red)) were evenly distributed within the glomerulus, monochromatic glomeruli developed as early as 4 days (FIG. 15B) after endothelial injury (L-NAME treatment) indicating the presence of single precursor cell-derived colonies. Note the presence of cells in multiple colors in the afferent arteriole (AA, arrow) at baseline (FIG. 15A) including one GFP+(green) and one RFP+(magenta) cell at the terminal segment, and the identically colored intra-glomerular cell colonies (mostly green, some magenta) 4 days later (FIG. 15B). FIG. 15C: Schematic of the three directly adjacent JGA cell types (MD, JG renin, and AA EPCs) forming a functional syntitium via cell-to-cell crosstalk to remodel the glomerulus. FIG. 15D-FIG. 15E: After two weeks washout of suboptimal tamoxifen induction, a few Confetti+ cells appear in glomeruli in stochastic distribution at baseline (FIG. 15D), but a high number of Confetti cells formed monochromatic tracing units (FIG. 15E) after subcapsular CCN1 treatment for one week.

FIG. 16. Systemic effects of renal CCN1 ablation. FIG. 16A-FIG. 16B: Plasma CCN1 levels after bilateral nephrectomy (BNx) in mice (FIG. 16A) determined using ELISA, and in rats (FIG. 16B) determined using plasma immunoblotting. Plasma samples were harvested before and after BNx at multiple times as indicated (n=5 animals each). FIG. 16B: Representative immunoblot and graph show the gradual decrease in plasma CCN1 levels after BNx. CCN1 was normalized to loading control (Coomassie blue) and baseline (value of 1.0). Data are average±SEM. *: p<0.05. FIG. 16C: TUNEL staining in brain and heart tissue sections of nNOS-CCN1 mice 3 weeks after tamoxifen.

FIG. 17. The effects of CCN1 and MMDD1 conditioned media treatment in the ADR mouse model of GS.

FIG. 18. MD-specific expression of CCN1 in the human kidney. FIG. 18D: Quantification of CCN1+MD cells in control (ctrl, n=6) and disease (CKD, n=4) kidney tissue. *: P<0.05.

FIG. 23. Establishment and features of new mouse (FIG. 23A-FIG. 23B) and human (FIG. 23C, FIG. 23D, FIG. 23E) macula densa primary cell cultures and immortalized cell lines.

FIG. 24. The robust protective effects of treatment with recombinant CCN1 or conditioned MD cell media in the BalbC Adriamycin mouse model of FSGS in vivo.

DETAILED DESCRIPTION

Figure 1:
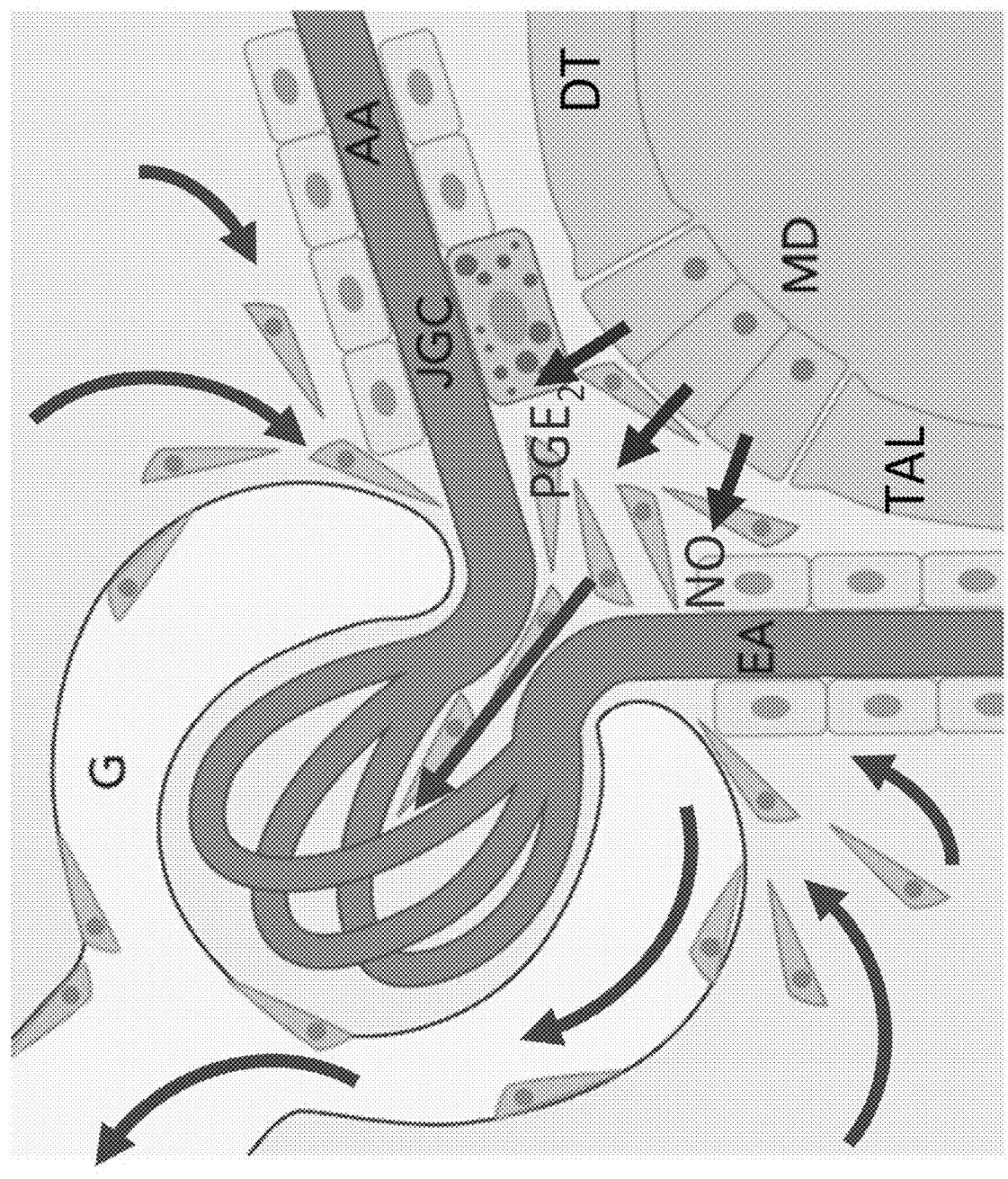
FIG. 1. Illustration of new, non-traditional angiogenic and glomerulotrophic roles of the MD which regulate renal interstitial, vascular, glomerular and tubular remodeling. Based on MD signals (red), NG2 (chondroitin sulfate proteoglycan)+ mesenchymal progenitor cells that reside in the renal interstitium (purple) proliferate and migrate towards the JGA area and differentiate into vascular cells (green) of the afferent (AA) and efferent (EA) arteriole (smooth muscle or renin-producing JG cell (JGC), mesangial cells, other glomerular (G) cell types, and tubular epithelia.

As described, MD cells are strategically localized at the glomerular entrance and an important cell type that function both as progenitors as well as organizers of nephron architecture. MD cells are part of the juxtaglomerular (JG) apparatus (JGA), a key anatomical site within the kidney that controls renal hemodynamics, glomerular filtration and the renin-angiotensin system (RAS). Classic, traditional functions of the MD and JGA are to help maintain body fluid and electrolyte homeostasis and blood pressure. These results build upon seminal contributions of the two main JGA mechanisms that perform these functions: tubular fluid flow and salt-dependent tubuloglomerular feedback (TGF) and renin secretion. Cyclooxygenase-2 (COX-2) and neural nitric oxide synthase (nNOS) are known MD-specific enzymes in the adult kidney, which via PGE2 and NO generation participate in key JGA functions. The paracrine actions of PGE2 via the EP4 receptor on the target cell is the well-established mechanism for not only MD-to-JG renin cell crosstalk (low salt-mediated renin/RAS activation), but also for stem and progenitor cell trafficking in many tissues. Interestingly, COX-2 and its products may be an important factor in nephrogenesis. Partial genetic knock-out and chemical inhibitors of COX-2 inhibit glomerulogenesis. Furthermore, preliminary work from the Inventors' lab found that COX-2 and nNOS products from MD cells mediate the migration and proliferation of NG2+ progenitors towards the JGA and glomerulus in conditions of strong RAS and MD stimulation (low salt diet+captopril). Thus, a single point source of PGE2 released from MD cells, which are strategically localized at the glomerular vascular entrance, may perform similar progenitor cell functions: migration and homing to the JGA. Therefore, MD cells may be important regulators of vasculo and glomerulogenesis during development, and vascular and glomerular remodeling in the adult kidney. The clinical relevance of the proposed new MD cell functions has been long-established: low dietary salt intake is part of the treatment for nephrotic syndrome (NS), focal segmental glomerulosclerosis (FSGS), and CKD. High dietary salt itself can cause relapse or worsening of NS. Dietary sodium restriction is known to improve CKD via blood pressure-independent glomerular structural changes. However, the exact mechanism of this beneficial effect of low salt intake has been unknown.

Recent studies highlighted the critical importance of chondroitin sulfate proteoglycan (NG2)-positive mesenchymal progenitor cells (also known as pericytes or activated myofibroblasts that reside in the renal interstitium) in vasculogenesis, the recruitment of and the association with the JG renin cell, but also in kidney fibrosis. Activated pericyte progenitors in the kidney express NG2. Importantly, NG2 has been used widely as a mesenchymal stem/stromal cell marker in several tissues and organs.

In addition to stem/progenitor cell-based regenerative approaches for CKD, the significance and therapeutic (translational) potential of identifying new mechanisms in renin (RAS) control as new therapeutic targets are enormous. Primary hypertension, a major risk factor for cardiovascular diseases, affects close to a third of the US population, and yet its (patho)physiology remains incompletely understood. The hormone renin is known to be clearly associated with hypertension as the rate limiting step of RAS activation, the primary means of long-term blood pressure regulation. Classic renal physiology knowledge is the dynamic transformation between JG cells and afferent arteriole vascular smooth muscle cells (VSMCs) based on homeostatic needs to maintain body fluid balance, but the origin, plasticity and fate of the JG renin cell is now challenged. As shown recently, mesenchymal stem cell-like cells and pericytes contribute to the recruitment of renin cells to the JGA, and renin cells are also precursors for parietal epithelial cells (PEC) and podocytes. These data are consistent with the presently proposed new MD functions.

The Inventors' new data make a high impact in renal and cardiovascular research and in the future clinical therapy of hypertension and glomerular kidney diseases. Several new, promising therapeutic targets have been identified for glomerular diseases and CKD that have been recently reviewed. However, the successful development of most of these approaches that target a specific, single molecular mechanism is uncertain. As a cutting edge area of research, regenerative medicine offers several stem/progenitor cell-based approaches to develop new treatments for kidney disease. Here the Inventors identified and characterized novel JGA functions, MD-mediated recruitment (homing) of mesenchymal progenitor cells to the JGA which is a robust and key novel mechanism of the induction and regulation of renal vascular, interstitial and glomerular remodeling. The Inventors expect that future work will identify several new therapeutic targets and support the future development of MD-targeting new regenerative therapeutic approaches for CKD.

The Inventors' new studies have addressed and solved a critical technical barrier in kidney research. A critical barrier in understanding the mechanistic details of kidney diseases has been the technical limitation to study critically important, but generally inaccessible renal cortical structures including the JGA and the glomerulus in their native environment in vivo. To date, most morphological and functional observations were based on cell culture or other in vitro models and fixed tissue sections. Modern cell fate tracking approaches also use only cross-sectional (at one time point rather than dynamic) histology techniques. Due to glomerular heterogeneity issues this is a serious technical limitation when studying dynamic renal processes. Consequently, the Inventors' knowledge on the plasticity of the same JGA/glomerular region over time, the migration properties of individual cells, the rate of the development of FSGS/albuminuria in one glomerulus, etc. in the intact kidney in vivo is very limited. However, during the past few years, breath-taking advances in the field of live imaging, in part due to the pioneering work by the Inventors' laboratory, have begun to revolutionize the field. Combining mouse genetics, bioinformatics with high-resolution fluorescence microscopy now allows insight into the biology of living renal cell types in the intact kidney in vivo in unprecedented detail. MPM is a powerful non-invasive imaging technique for the deep optical sectioning of living tissues. The basic principles, applications, advantages, and limitations of this imaging technology for the study of the living intact kidney including the GFB have been recently described in detail. The first applications of MPM of the intact living kidney were subsequently improved to directly and quantitatively visualize the permeability of the GFB to albumin and cell motility/migration in health and disease in vivo. The use of future, ever-developing imaging techniques and approaches (e.g. long wavelength infrared lasers, extremely sensitive detectors, super-resolution nanoscopy) are expected to further push the limits of intravital, functional kidney imaging. Serial MPM of novel NG2+ progenitor, MD and JG cell mouse models with fluorescent lineage tags is a novel, unique, state-of-the-art imaging approach that the Inventors used to directly and quantitatively visualize the recruitment and fate of renal mesenchymal progenitor cells in vivo and to study the novel role of MD cells as inducers and master regulators of renal vascular and glomerular remodeling in health and disease.

A key innovation is the identification and characterization of new, non-traditional mechanisms and role of MD cells in renal tissue remodeling. These studies are expected to result in paradigm-shifting discoveries regarding new JGA functions in health and disease. The Inventors expect that functional characterization and better understanding of the regulation of MD cell gene profile will identify several novel MD-specific genes and MD-derived paracrine factors which may be further developed in the future as new regenerative therapeutic targets for the better treatment of cardiovascular and kidney diseases.

New advances in stem/progenitor cell research has brought a new perspective and focus on tissue regeneration and cell fate changes in several areas of the biomedical sciences including renal and cardiovascular (patho)physiology. Novel technologies have become available for fluorescent tagging of cell lineage and individual cell fate tracking in various organs in a way that has not been possible before. As another innovation, the Inventors applied these amazing research tools in combination with a unique imaging approach pioneered in part by the Inventors' laboratory and the first-ever MD bioinformatics approach to advance the Inventors' understanding of the functions and fate of MD and JG cells which are critical components of the RAS, and important regulators of renal and glomerular functions. Serial multiphoton microscopy (MPM) of the same area of the intact mouse kidney in vivo over several days, which is an important technological breakthrough, was performed to track the fate and function of the same, individually marked NG2+ mesenchymal progenitor cell and JG renin cell in response to physiological and pathological challenges, and to study the role of MD cells in cellular remodeling of the renal tissue. In vivo cell fate tracking was combined with quantitative MPM imaging of the basic functions in renal (patho)physiology in the intact whole kidney which the Inventors pioneered during the past years including changes in single nephron filtration rate (SNGFR), blood flow and tubular flow, albumin permeability of the glomerular filtration barrier, renin granule content, release, and tissue renin activity.

Another innovation in the Inventors' work is the development of new transgenic mouse models in which the NG2+ mesenchymal progenitor, JG renin, and MD cell lineages have been fluorescently tagged. These models helped the Inventors to specifically label, manipulate (ablate) MD cells in vivo in the intact kidney and analyze their role in renal vascular and glomerular remodeling. Also, the Inventors were able to properly identify and track over time the migration of individual NG2+ mesenchymal progenitor and JG renin cells within the renal interstitium, vasculature and glomerulus over time together with simultaneous portrayal of the changes in renal function. In summary, the combination of the Inventors' laboratory's expertise in MPM and several new mouse models complemented with highly popular and powerful molecular and cell techniques (gene profiling, microarrays, RNA sequencing) is a unique and novel approach that the Inventors used to test key questions about the groundbreaking new role of MD cells in JGA function in health and disease.

Described herein is composition including a peptide and a nucleic acid. In other embodiments, the peptide includes a homing peptide. In other embodiments, the peptide includes a histidine-rich amphiphatic peptide. In other embodiments, the homing peptide is capable of specifically binding to macula densa (MD) cells. In other embodiments, the nucleic acid is bound to the peptide. In other embodiments, the nucleic acid is a microRNA. In other embodiments, the microRNA includes miR-30 and/or miR-541. In other embodiments, the peptide includes the amino acid sequence SEQ ID NO:1. In other embodiments, the peptide includes an amino acid sequence with 70-75%, 75-80%, 80-85%, 85-90%, 95% or great sequence identity to SEQ ID NO:1. Further described herein is a pharmaceutical composition including the aforementioned composition and a pharmaceutically acceptable carrier. This application includes SEQ ID NO: 1

Also described herein is a method of treating a kidney disease and/or condition including administering to a subject, a pharmaceutical composition including a peptide, a nucleic acid, and a pharmaceutically acceptable carrier. In other embodiments, the kidney disease includes chronic kidney disease. In other embodiments, the peptide is a fusiogenic peptide including a homing peptide and a histidine-rich amphiphatic peptide. In other embodiments, the fusiogenic peptide includes the amino acid sequence SEQ ID NO:1. In other embodiments, the peptide includes an amino acid sequence with 70-75%, 75-80%, 80-85%, 85-90%, 95% or great sequence identity to SEQ ID NO:1. In other embodiments, the nucleic acid is a microRNA. In other embodiments, the microRNA includes miR-30 and/or miR-541. In various embodiments, treatment includes improvements in kidney function, as shown by a decline in albuminuria, reduced glomerulosclerosis and fibrosis.

Further described herein is a composition including a recombinant CCN family member 1 (CCN1) peptide. In other embodiments, the recombinant CCN1 peptide includes a homing peptide. Also described herein is a method of treatment including administration of a composition including a recombinant CCN1 peptide. In various embodiments, treatment includes improvements in kidney function, as shown by a decline in albuminuria, reduced glomerulosclerosis and fibrosis.

Further described herein is a composition including media conditioned by macula densa (md) cells. Also described herein is a method of treatment including administration of a composition including media conditioned by macula densa cells. In various embodiments, treatment includes improvements in kidney function, as shown by a decline in albuminuria, reduced glomerulosclerosis and fibrosis.

Further described herein is a method of treating a kidney disease and/or condition including administering to a subject, a therapeutically effective dose of a loop diuretic. In other embodiments, the loop diuretic includes furosemide, analogs and derivatives thereof. In other embodiments, the therapeutically effective dose activates macula densa (md) cellular repair.

Also described herein is are a composition including macula densa (md) cells. In various embodiments, the md cells include CCN1 in vesicle cargo. In various embodiments, the md cells are capable of paracrine effects on vascular mesangial cell types. In various embodiments, the md cells are capable of serial passaging as a cell line.

Example 1

Functional Characterization of the Novel Renal Tissue Remodeling Function of MD Cell This study investigated whether MD cells can induce the mobilization, proliferation, and recruitment (homing) of renal mesenchymal progenitor cells into the JGA, to facilitate vascular and glomerular tissue remodeling. The effects of in vivo MD cell activation (low salt diet+ACEI) or blockade (in vivo cell ablation, selective COX-2 and nNOS inhibitors) on kidney tissue structure and function were studied using new transgenic mouse models (NG2-Tomato/Confetti, MD-GFP, MD-DTA). Regulation of MD fingerprint in stimulated states were analyzed by performing MD cell harvesting, isolation, transcriptome analysis and bioinformatics.

A critical barrier in understanding the true nature and functions of MD cells has been the technical limitation to study this critically important, but generally inaccessible therefore mysterious cell type in its native environment in vivo. To date, most morphological and functional observations were based on cell culture or other in vitro models, fixed histological sections or using indirect in vivo approaches. Therefore, the Inventors' knowledge is limited to their classical role in the regulation of renal hemodynamics, GFR, and renin secretion. However, new preliminary data point to the much more complex role of MD cells, with several non-traditional functions in renal tissue remodeling and maintenance (FIGS. 2-10). For a (patho)physiologist it is not surprising that the clues regarding true kidney "regenerative" mechanisms (in contrast to the many non-specific, single cell-level "recovery" mechanisms identified so far) come from classic physiological knowledge and JGA function. The described tissue remodeling function of MD cells is very consistent with the other, classic JGA functions, and with the adaptive changes in kidney structure and function during evolution, and embryonic organogenesis. In the cutting edge area of research on kidney regeneration, a variety of experimental kidney injury models, ischemia-reperfusion, chemical toxins, and surgical methods have been applied to study regeneration, but none of these injury models actually generate kidney-specific signals to trigger tissue repair. The most robust and organ-specific physiological stimulus is the loss of body fluid and salt, and MD cells are the most important salt-sensing cell types involved in the body's response to this condition. Therefore, the Inventors believe that the MD and JGA is where the Inventors can look for finding a master program of kidney tissue remodeling and regeneration.

New preliminary data show MD-specificity of secreted angiogenic peptides (FIG. 9) that are known to be critically important in tissue remodeling in other organs. Also, new data using MD-DTA mice show that MD cell ablation alters renal vascular remodeling (FIG. 4). Further, another newly established mouse model (MD-Confetti) revealed that MD cells are progenitor cells and contribute to nephron formation during kidney development (FIG. 5). Together with their strategic anatomical localization at the glomerular vascular entrance (relevant to embryonic nephrogenesis), MD COX-2 and nNOS-dependent (MD-specific enzymes in the adult kidney) NG2 cell proliferation and migration towards the MD (FIGS. 6-7), angiogenic, cell growth, development, differentiation, and patterning gene profile (FIG. 8), these new data strongly support the proposed non-traditional, tissue remodeling functions of the MD.

Example 2

Track the Fate and Migration Characteristics of NG2 Cells in Normal and MD-Stimulated Kidneys These studies applied genetic cell fate-mapping strategies in new transgenic mice that report for cells of the NG2+ progenitor (NG2-Tomato and Confetti), or alternatively the renin lineage (Ren1d-Confetti) to test if MD stimulating conditions augment the proliferation and migration (homing) of NG2+ cells into the JGA and their recruitment and differentiation into AA vascular smooth muscle, JG renin, mesangial cells, glomerular epithelial cells (both podocytes and PECs), and proximal tubular cells. Adult (6-8 weeks of age), previously tamoxifen-induced (2-3 weeks tamoxifen washout) NG2CreER-Tomato or Confetti mice received low salt+captopril treatment for one week, using sodium deficient diet (from Harlan Teklad, Cat #TD 90228) and 200 mg/L ACE inhibitor captopril in drinking water ad libitum (a well-established strong stimulus to activate the MD and RAS). Control age-matched mice received only vehicle (n=6 each group). Animals were used for serial MPM imaging and/or euthanized and tissues collected at one week endpoint.

The Inventors' signature visual approach, in vivo serial MPM imaging of intact kidneys in vivo was performed as described before using a Leica SP5 multiphoton confocal fluorescence imaging system (DMI 6000 inverted microscope and Coherent Chameleon Ultra-II MP laser).

Example 3

Animal Models

In preliminary work the Inventors established several new transgenic animal models and experimental approaches (FIGS. 2-10), these are:
1. Md-GFP Mice.

The Inventors developed and successfully established intravital MPM imaging of nNOSCreERT2-KI/Tomato$^{floxS}$-

TOPGFP (inducible MD-GFP) mice which in the renal cortex specifically express the intensely green fluorescent protein GFP in MD cells. These mice were created by intercrossing nNOS-CreERT2-KI[38] (mice with nNOS promoter-driven, tamoxifen-inducible expression of Cre recombinase (knock-in model) which in the renal cortex provides 100% MD-specific Cre expression) and Tomato$^{floxSTOP}$GFP (B6.129 (Cg)-Gt(ROSA)26Sor$^{tm4(ACTB-tdTomato,-EGFP)Luo}$) mice (both from JAX). These animals express tomato in all cells at baseline. After Cre-mediated excision the Cre-expressing cell lineage will however express the membrane targeted GFP protein (FIG. 8A). MD-GFP mice showed no morphological or functional abnormalities compared to WT mice (not shown). A few cells scattered through the inner medullary collecting duct also showed GFP labeling (not shown). Since this is a knock-in model, only heterozygous nNOSCreERT2-KI mice were used in all experiments. Intact MD nNOS activity was confirmed using NADPH-diaphorase staining.

2. NG2-Tomato and Confetti Mice.

These mice have been successfully generated in the Inventors' lab (FIGS. 2-3, 10) by intercrossing NG2CreER BAC transgenic mice which express a tamoxifen-inducible Cre recombinase under the control of the mouse NG2 (Cspg4) promoter/enhancer[39] and mice expressing the R26R-Tomato or Confetti construct[40] (both from JAX) resulting in the NG2 cell-specific expression of either membrane-targeted CFP, nuclear GFP, cytosolic YFP/RFP. Constitutive NG2-DsRed mice are also available (FIG. 2A).

3. Ren1d-Confetti Mice.

The Inventors developed and successfully established intravital MPM imaging of these mice (FIG. 2E) which express the Confetti reporter construct in cells of the Ren1d lineage. These mice were created by intercrossing Ren1dCre mice (received from Dr. Ariel Gomez with established MTA) and mice expressing the R26R-Confetti construct (from JAX). Inducible Ren1cCreER-Confetti mice are available from Dr. Gross.

4. MD-DTA Mice.

These mice have been successfully generated in the Inventors' lab by intercrossing nNOS-CreERT2-KI mice with ROSA26-eGFP-DTA mice (both from JAX). Administration of tamoxifen to these mice induced diphtheria toxin A expression in cells expressing nNOS, which in the renal cortex specifically ablated MD cells. This approach is similar to the one used recently for ablating JG renin cells. This is an important new mouse model to test, in general, the role of MD cells in vascular/glomerular remodeling in vivo. Because of the considerable nNOS expression in other organs including the brain (and the patchy expression in the renal medulla) the Inventors successfully developed local, subcapsular tamoxifen injection (pellets), and are carefully monitoring the development of non-related phenotypes and side-effects. Nevertheless, the Inventors are encouraged by the viability and renal phenotypes of the nNOS knockout mouse model and by the preliminary data (FIG. 4).

The feasibility of routinely performing MPM imaging of glomeruli in the intact C57BL6 mouse kidney is shown by the preliminary data (FIG. 2). It has been also confirmed by at least three independent laboratories. Serial MPM imaging of the same inducible NG2-Tomato mouse kidney at baseline, and 1 and 2 weeks after low salt diet+captopril treatment revealed the migration of NG2+ cells towards the MD and into the glomerular mesangium, visceral and parietal epithelial layers, and into the early proximal tubule (FIGS. 2-3). These data support the notion that NG2 cell recruitment to the AA, JGA and glomerulus can significantly and rapidly contribute to the remodeling of these anatomical structures under MD stimulating conditions. Supplement movie 1 shows in vivo MPM imaging (Z-sectioning) of a NG2-Tomato kidney 1 week after low salt+ACEI diet.

Initial testing of the newly established MD-DTA mouse model (FIG. 4) confirmed the successful, inducible, in vivo ablation of MD cells in the intact kidney using a single subcapsular tamoxifen injection. MD-DTA mice were viable, appeared normal, and were able to maintain blood pressure during the first week after tamoxifen, supporting the feasibility of the proposed chronic cell fate-tracking experiments. Importantly, the Inventors observed the decreased number of JG renin cells in these tamoxifen-induced mice compared to non-induced controls (FIG. 4C-D). These new findings support the Inventors' hypothesis on the new, non-traditional functions of MD cells and show that this critically important experimental model is working: MD cell ablation alters renal vascular remodeling. In addition, new data showed that MD cells are progenitor cells and contribute to nephron formation during kidney development (FIG. 5). MD cell lineage tracing experiments in vivo using tamoxifen-inducible MD-Confetti mice found exclusively clonal (i.e. single-color) multi-cell tracing units in thick ascending limbs (TALs). These new studies identified MD cells as a stem/progenitor population within nascent nephrons dedicated to generating the TAL of Henle's loop. Although this new MD cell function will not be further explored in the present proposal, these data clearly support new, non-traditional functions of MD cells that are consistent with renal tissue remodeling.

Example 4

Test Whether Classical MD Autocoids PGE2 and NO Play a Role in NG2 Cell Recruitment In other preliminary experiments NG2, Ki67, and renin immunofluorescence found a significantly increased number of NG2+ proliferating cells in the MD area with partial co-localization with renin in response to low salt diet+captopril treatment (a well-known strong RAS and MD stimulus) for one week (FIGS. 6-7). The increased density of NG2+ cells was 70% inhibited by the administration of the selective COX-2 inhibitor SC58236 (FIG. 6E). Also, the selective nNOS inhibitor 7-NI completely abolished the proliferation of NG2+ cells (FIG. 7E). Since COX-2 and nNOS are MD-specific enzymes in the renal cortex, these data show critical support for the notion that MD cells via paracrine factors are important regulators of mesenchymal progenitor cell recruitment to the JGA interstitium, vasculature, and glomerulus.

Example 5

Examine the Regulation of the MD Angiogenic Gene Networks in MD-Stimulated and CKD Kidneys The Inventors have established the differential display (regulation) of MD gene regulatory networks by comparison of the MD molecular fingerprint in control age-matched MD-GFP mice and after one week of low salt+ACEI treatment (n=3 mice each, total of 18 samples: green MD cells, control red cells, and whole kidney from control and low salt+ACEI kidneys). Based on the Inventors' preliminary data (FIGS. 8-9) the Inventors focused on genes involved in angiogenesis (such as the CCN family), cell growth, development, guidance, and extracellular matrix remodeling, and their regulatory networks. Approach is similar to those used for other renal epithelia, e.g. podocytes. Approach was complemented with conventional IHC/WB analysis of MD factors on the protein level using ctrl and low salt+ACEI kidneys from both healthy and CKD mice.

To better understand the molecular mechanisms and players in these novel MD cell functions, in preliminary studies the Inventors developed a new MD-GFP mouse with MD-specific expression of Cre recombinase and/or GFP. GFP-labeled MD cells (green) and Tomato-labeled adjacent tubular epithelial cells of the distal nephron (red) were FACS sorted from freshly digested kidneys of mice with MD-specific expression of GFP and their RNA isolated (FIG. 8). Microarrays confirmed high expression of known MD-specific genes (nNOS, Ptgs2 (COX2), Fxyd2, Atp4a, Slc29a1, and the control GFP) and identified new MD-enriched genes (compared to red cells which are adjacent distal nephron epithelia, and total kidney cortex) including Pappa2, Cyr61, Mmp14, Klk1b22, Wnt10a, Bmp3, Hoxb2, Thsd4, Angptl7, Robo2, Slit2, Ngfr, etc.) that play important roles in angiogenesis, cell growth, development, guidance, and extracellular matrix remodeling. These were very unexpected findings and provided further support for view that MD cells are important angiogenic and trophic cells and via several novel paracrine factors MD cells play new roles in the maintenance and remodeling of the renal interstitium, vasculature, and glomerulus.

Figure 9:
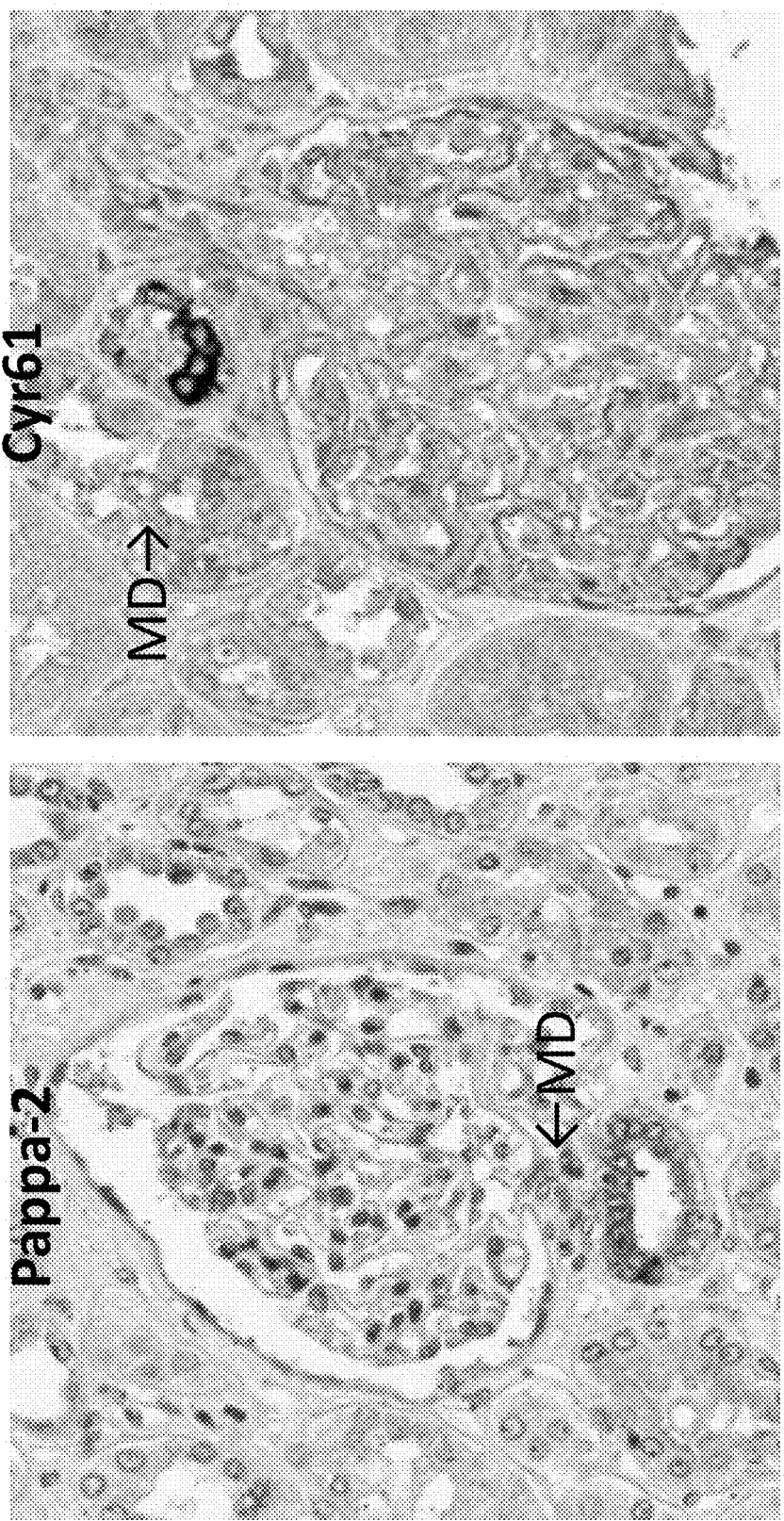
FIG. 9. High expression of novel angiogenic secreted proteins in cells of the macula densa. Immunohistochemistry of control human kidney tissue sections found strong immunolabeling for Pappa-2 (Pregnancy-associated plasma protein A2) and Cyr61 (Cystein-rich protein 61) in MD cells, compared to other renal cell types. Modified from The Human Protein Atlas database. The Inventors' laboratory has confirmed the same MD-specific expression pattern and up-regulation by low salt+ACEI diet for one week in the mouse kidney (not shown).

Some of the top MD-enriched gene networks newly identified by these MD cell microarrays were Pappa2 and the CCN gene family (150-fold enrichment in MD cells compared to control red cells), which are known to be critically important and involved in angiogenesis, extracellular matrix, and tissue remodeling in other organs. Secreted CCN proteins include cystein rich protein 61 (Cyr61), a potent inducer of angiogenesis, cell adhesion, migration, differentiation in a cell type and context-dependent manner. Other members include connective tissue growth factor (CTGF), nephroblastoma overexpressed (Nov), Wnt-induced secreted proteins (WISP1-3), Pappa-2 (Pregnancy-associated plasma protein A2), etc. FIG. 9 confirms the high expression and MD specificity of some of these angiogenic secreted proteins in the human kidney.

Example 6

Discussion

These experiments support the described non-traditional roles of MD cells as master regulators of renal interstitial, vascular and glomerular remodeling. Also, the Inventors' studies identified NG2+ cells as an important subpopulation of interstitial mesenchymal progenitors as the origin of the newly recruited interstitial pericytes, VSMC, JG and glomerular and tubular epithelial cells. Moreover, MD-mediated NG2 cell reactivation, proliferation, and recruitment to the vasculature, JGA and glomerulus was highly active in response to the MD stimulating low salt+ACEI treatment compared to controls (as shown in FIG. 10). Localization, density, clonality, and final fate of NG2+ cells (number of cells within single-color multi-cell tracing units, further indicating NG2 proliferation and single cell-derived progenies, see FIG. 2F) further supported their migration towards the MD epicenter, homing to the JGA, and differentiation into arteriolar VSMCs, renin cells, mesangial cells, podocytes, PECs, and proximal tubule epithelia. This was confirmed by the co-localization of genetic NG2 lineage tag Tomato (or Confetti) and cell-specific markers using immunofluorescence (as shown in FIG. 3). The Inventors found the appearance of increased number of clonal (i.e. monochromatic) cell groups (progenies) of NG2 cell lineage in vascular, JGA, and glomerular tissue regions in low salt+ACEI compared to control groups. Preliminary data showed (FIGS. 4, 6-7) that MD ablation, COX-2 and nNOS blockade inhibited low salt+ACEI-induced NG2 cell proliferation and migration. Also, these studies further confirmed MD-enrichment and up-regulation of several novel angiogenic genes (e.g. CCN family) with potential differential regulation and roles in CKD. These include Cyr61, Pappa2, Ngfr, Bmp3, Wnt10a, Angptl7 as well as others (FIG. 8D) which are known to be critical in development, cell growth, guidance and patterning. The expression of these genes is consistent with the view that MD cells can induce and regulate the activation, migration, and recruitment of mesenchymal progenitors into the renal interstitium, vasculature, JGA and glomerulus. The precise knowledge of upregulated (or differentially regulated) MD genes during MD-stimulating low salt+ACEI conditions will help to develop novel therapeutic approaches for CKD. One alternative approach is to combine mRNA and miRNA transcriptional profiling with quantitative proteomic analyses (mass spectrometry) on freshly isolated MD cells, and use bioinformatics to functionally analyze all obtained data. A more complex 'omics' approach would facilitate the discovery and integration of novel gene, protein, and organelle regulatory networks that would deepen the Inventors' systematic understanding of MD cell biology.

Example 7

Examine the Effects of MD Activation on Kidney Structure and Function in CKD This investigated whether the development of CKD pathology can be prevented or ameliorated by MD activation. The protective effect of MD stimulation on kidney structure/function, the augmented migration and differentiation of resident renal mesenchymal stem cells into mesangial, and glomerular/tubular epithelial cells was tested in new transgenic mice combined with a model of focal segmental glomerulosclerosis (FSGS) using serial MPM of the same glomeruli over several days (cell fate tracking, SNGFR, albumin leakage measurements), and conventional phenotyping methods (albuminuria, histology, GS score).

Background and rationale: The newly acquired knowledge on MD cells and their new functions (FIGS. 2-10) suggest that these cells may play an important role in glomerular disease, and that targeting and augmenting MD mechanisms may improve FSGS pathology. Studies suggest that renal interstitial mesenchymal progenitor cells (a.k.a. pericytes and myofibroblasts) can also be involved in renal pathology and fibrosis. However, when precisely controlled by the new MD glomerulotrophic mechanisms, resident mesenchymal progenitor (NG2) cells may be used for protective, regenerative purposes. This translational aim tested if robust MD activation via their novel glomerulotrophic function can provide therapeutic benefit in FSGS via the induction of glomerular recruitment of NG2+ progenitor cells and augmented glomerular cellular and extracellular matrix remodeling, as described. The clinical relevance of the proposed new MD cell functions has been long-established: low dietary salt intake is part of the treatment for nephrotic syndrome (NS), FSGS, and CKD. High dietary salt itself can cause relapse or worsening of NS. Dietary sodium restriction is known to improve CKD via blood pressure-independent glomerular structural changes. The Inventors' studies have helped to identify the underlying mechanism which has been elusive.

In preliminary studies the Inventors tested the effects of robust MD cell stimulation by low salt+ACEI treatment on NG2+ cell density (FIG. 10). Compared to the very few NG2+ cells (13±3) localized in the JGA/glomerular area in the non-treated control kidney (FIG. 10A), the Inventors observed a 5-fold increase in NG2+ cell density (64±7) in the renal cortex (mainly in JGA/glomerular areas) after low salt+ACEI treatment for one week (FIG. 10B-C). These data further suggest that strong MD stimulation is associated with highly active tissue remodeling by NG2+ cells in the renal cortex, including within the glomerulus.

Example 8

Expected Results, Interpretation

The Inventors expect that FSGS pathology will be improved by MD stimulation (low salt+ACEI) due to augmented glomerular cellular and matrix remodeling. This will be reflected by increased glomerular density of cells that belong to the NG2 lineage, reduced albumin leakage, albuminuria, sclerosis marker expression, and improved GS scores. In mice with MD cell ablation, FSGS pathology will not improve or will even worsen. One potential, far-reaching interpretation of the new results is that MD dysfunction may be an important factor, the "root cause" of glomerular pathologies. Compromised MD-specific regenerative mechanisms may be brought on by the high salt containing western diet, and other environmental aspects (MD cells also detect tissue metabolism, tubular flow, etc). Future work will fine-tune the presently used broad-strokes MD activation approach (low salt+ACEI) by specifically targeting the most critical angiogenic and glomerulotrophic genes only in MD cells, and establish the best treatment regimen (e.g. one-week temporary versus prolonged stimulation) in future preclinical studies. There are several alternatives the Inventors may consider for MD stimulation (e.g. loop diuretics), or MD blockade (selective COX-2 and nNOS inhibitors, laser ablation), or NG2 cell tracking (immunolabeling, models with constitutive genetic label) as proposed. Since MD cells perform critical functions in the control of renal hemodynamics and RAS, the Inventors will carefully monitor changes in overall kidney function and will apply partial MD cell ablation (by controlling tamoxifen dose) as necessary. Nevertheless, preliminary data are encouraging (FIG. 4). The proposed animal models require the generation and breeding of mice with multiple transgenes which takes time. However, all of the proposed mouse models have been already generated in the Inventors' laboratory at USC. The existing mouse colonies are breeding well and the Inventors do not expect problems with animal numbers. Although the preliminary data strongly support the role of NG2+ progenitor cells, the Inventors are ready to use alternative mouse models of labeled mesenchymal progenitor cell populations, e.g. Col1GFP or Foxd1-Cre (which are available at USC). Although the final NG2 cell fate will be determined as proposed (FIG. 3), MPM imaging has the necessary optical resolution to identify NG2 cell lineage, e.g. podocyte ultrastructure (foot processes) can be visualized optically using MPM.

Example 9

Study of the Role and Effects of CCN1 in Maintaining Glomerular Capillary Structure and Function This study investigated whether sustained activity of CCN1-mediated angiogenic mechanisms in the JGA are critically important in maintaining the integrity of glomerular endothelial cells (GEnCs), and the normal glomerular structure and function. The effects of CCN1 will be studied using in vitro angiogenesis assays, and new in vivo transgenic mouse models (inducible JGA-specific conditional CCN1 KO mice). The Inventors also tested the hypothesis that in addition to its local glomerular effects, CCN1 produced in the JGA is released into the blood and serves as a novel systemic hormone promoting general cardiovascular (CV) health. Finally, for therapeutic development purposes, the Inventors tested whether established CKD pathology can be improved by treatment with exogenous CCN1. The protective effect of CCN1 treatment on kidney structure and function was tested in animal models of CKD.

Aiming to better understand the dynamics of cellular remodeling of the glomerulus in vivo, the Inventors' laboratory has recently developed new transgenic mouse models with fluorescent lineage tags, and a novel intravital imaging approach to study and track the fate and function of various glomerular cell types including podocytes and resident mesenchymal progenitor (NG2+) cell-derived cell types. Since complete glomerular remodeling also requires the contribution of the endothelium and endothelial progenitor cells, the Inventors initiated a new line of investigation to study angiogenic mechanisms of the glomerulus and to explore the specific role of CCN1. In parallel, gene profiling studies of the JGA showed that one of the top enriched, new JGA-specific genes in the mouse kidney was the angiogenic inducer CCN1. As described below, the Inventors generated multiple lines of supporting preliminary data that suggest JGA-derived CCN1 functioning as a major regulator of the glomerular endothelium and in the maintenance of glomerular vascular integrity in the adult kidney.

CCN1 (also known as cysteine-rich protein Cyr61) is a member of the CCN family of secreted matricellular proteins that includes connective tissue growth factor (CTGF, CCN2), nephroblastoma overexpressed (NOV, CCN3), Wnt1-Inducible signaling protein 1 (WISP-1, CCN4), WISP-2 (CCN5), and WISP-3 (CCN6). First identified as the product of a growth factor-inducible immediate-early gene, CCN1 is an extracellular matrix-associated angiogenic inducer that functions as a ligand of integrin receptors to promote the adhesion, migration, proliferation, differentiation, and survival of primarily vascular endothelial cells, but also fibroblasts. CCN1 is involved in the transduction and modulation of growth factor and hormone signaling and in sensing the extracellular environment, as the CCN1 gene is rapidly activated at the transcriptional level when the target cells are stimulated with serum growth factors such as fibroblast growth factor (FGF), PDGF, and TGFβ, or by various environmental stresses (hypoxia, mechanical stretch). Reflecting on their functions, CCN proteins are organized into four conserved modular domains that share sequence similarities with IGF-binding proteins (IGFBPs) (role in growth factor binding), the von Willebrand factor type C repeat (role in oligomerization), the thrombospondin type 1 repeat (role in extracellular matrix protein interactions), and the carboxyl terminal cysteine knot that is typical of several extracellular mosaic proteins (role in dimerization). As an adhesion substrate, CCN1 promotes cell spreading and adhesive signaling, resulting in the activation of focal adhesion kinase, paxillin, and Rac. CCN1 can regulate the expression of genes involved in angiogenesis and matrix remodeling, including VEGF-A, VEGF-C, type I collagen, matrix metalloproteinase 1 (MMP1), and MMP3. Mechanistically, CCN1 functions as a ligand of multiple integrin receptors, including integrins $\alpha_v\beta_3$, $\alpha_v\beta_5$, $\alpha_6\beta_1$, $\alpha_{IIb}\beta_3$, and $\alpha_M\beta_2$, which mediate many of its activities in various cell types. Also, CCN1 can bind to heparan sulfate proteoglycans (HSPGs) including syndecan-4. All of the CCN1-associated molecules mentioned in this paragraph have confirmed roles in various glomerular functions and pathology, suggesting that CCN1 may be centrally involved in glomerular vascular biology and (patho)physiology.

CCN1 has been associated with a variety of physiological processes (angiogenesis, wound healing, tissue repair, embryonic development, placenta growth and vascularization), however aberrant CCN1 expression has also been linked to a variety of diseases such as chronic inflammation, liver fibrosis, rheumatoid arthritis, atherosclerosis, retinopathy, and many different forms of cancer. However, the specific roles of CCN1 in the normal kidney, and in the development of CKD are largely unknown or unclear, in part thanks to conflicting reports. A few studies reported the specific localization and acute and temporary upregulation of CCN1 in the proximal tubule by acute kidney injury, lupus, and obstructive kidney injury, while other studies reported its exclusive expression in podocytes. Antibody specificity issues, species difference, the lack of gene-level confirmation, and studying only temporary expression of an inducible gene at otherwise non-specific cell types were likely the reasons for the conflicting data published in earlier literature. Importantly, none of the previous studies have detected the robust and constitutive (!) expression of CCN1 in the JGA, which is most effective and relevant for the regulation of glomerular endothelium and vasculature.

The proposed study has great potential to make a high impact in kidney/CKD research and in the future clinical diagnostics and therapy of glomerular kidney diseases. Several new, promising therapeutic targets have been identified for glomerular diseases and CKD that have been recently reviewed. However, the successful development of most of these approaches that target a specific, single molecular mechanism is uncertain. As detailed above, CCN1 appears to be centrally involved in a complex array of molecular and cell-based glomerular tissue remodeling mechanisms. Investigating the role and mechanisms of CCN1 signaling, which appears to be key and specific for maintaining the structural and functional integrity of the glomerulus, will be a significant step in the Inventors' better understanding of the complex pathomechanism of CKD, and to translate this information to the clinic. In fact, the Inventors' work to target CCN1 support future development of new, and glomerulus-specific non-invasive clinical diagnostic and therapeutic approaches for CKD.

New preliminary data show that exogenous CCN1 added to the media of cultured GEnCs produced a robust dose-dependent effect on cell proliferation and migration. CCN1 appeared to be more effective on in vitro angiogenesis (tube formation assay) than the gold-standard VEGF (FIG. 11). Other classic in vitro assays of GEnC cell proliferation and cell migration (scratch opening assay) showed similar robust effects of CCN1 (not shown). The effects of CCN1 were almost completely abolished in presence of blocking antibodies for integrins $\alpha_v\beta_{33}$ and VEGF receptor blockers (not shown b/c space limitations), suggesting that CCN1 is an important amplifier of growth factor and adhesion signaling and effect on GEnCs. CCN1 had no effect on renin cell proliferation and migration (not shown).

Figure 18C:
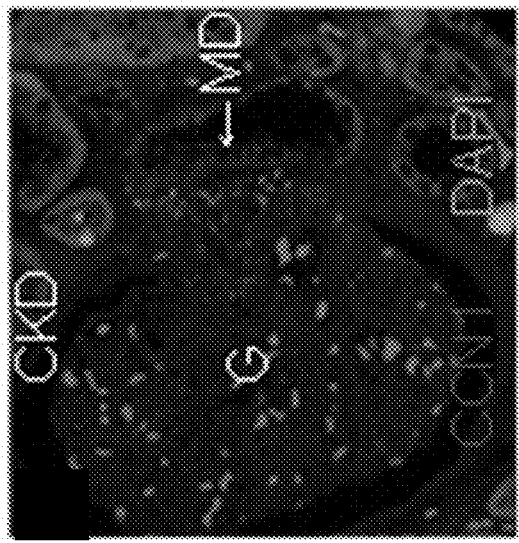
FIG. 18B, FIG. 18C, FIG. 18D: CCN1 immunofluorescence in nephrectomy tissue of healthy control (FIG. 18B) and CKD patients (FIG. 18C).
Figure 18B:
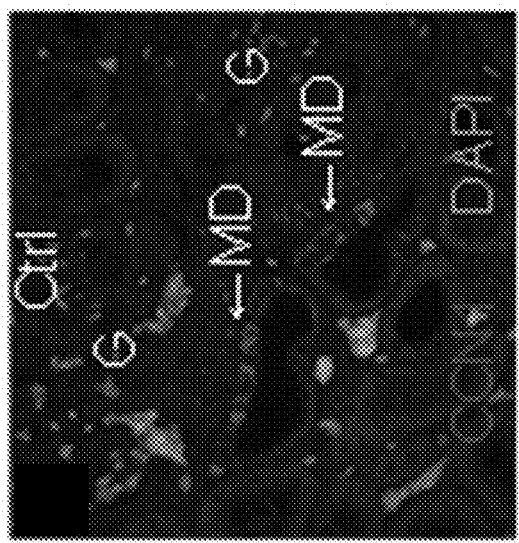
Figure 18A:
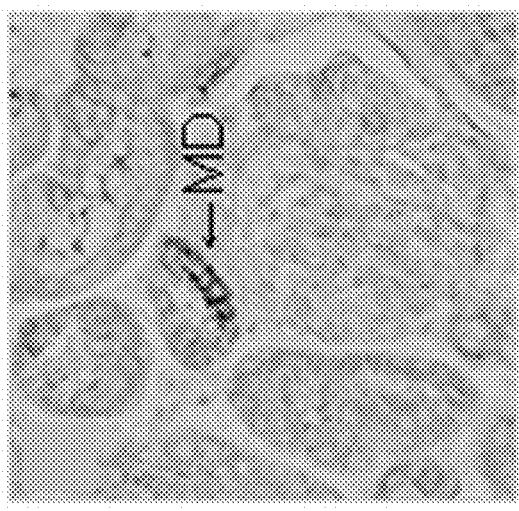
FIG. 18A: Immunoperoxidase labeling of CCN1 shows strong CCN1 expression exclusively in cells of the macula densa (MD).

The Inventors' previous, unpublished gene profiling data suggested CCN1 as a highly expressed JGA-specific gene. This finding was quickly confirmed on the protein level in the human kidney using the online Human Protein Atlas database (FIG. 12A), and in a much cleaner version recently in the Inventors' own laboratory (FIG. 18A-C). JGA-specific CCN1 expression in the mouse kidney was confirmed using genetic (CCN1-GFP mice) and immunological tools (FIG. 12). This was necessary because of specificity issues of several commercial CCN1 antibodies.

Next, the Inventors generated new transgenic mice with both constitutive and inducible Cre-lox based deletion of CCN1 from JG renin and MD cells. FIG. 13 shows that in heterozygous Ren1d-Cre/CCN1fl mice (constitutive Cre), kidney tissue harvested from 4-weeks-old animals showed grossly distorted glomerular morphology in most glomeruli (dilated single capillaries, few endothelial cells but mesangial expansion). Similarly, inducible MD-CCN1 KO mice (6-8 weeks of age) started to develop ++/+++ albuminuria 3 weeks after tamoxifen induction, and interestingly, systemic growth retardation as well (not shown).

Figure 14:
FIG. 14. CCN1 expression in the human embryonic kidney. CCN1 immunofluorescence (red) in 18-20 weeks of gestation identified significant CCN1 expression in S-shaped bodies of the developing human kidney. CCN1 labeling was highest in center-portions of S-shaped bodies (arrow) where the ingrowth of stromal mesenchymal cells are known to generate the mesangium and glomerular arterioles. Nuclei were labeled with DAPI (blue).

The embryonic developmental and human translation relevance of constitutive CCN1 expression in the JGA was demonstrated in preliminary IF localization of CCN1 in the developing human embryonic kidney (FIG. 14). Significant CCN1 expression was found in center-portions of S-shaped bodies where the ingrowth of stromal mesenchymal cells are known to generate the mesangium and glomerular arterioles. This suggests that similarly to the well-established factors including VEGF and Angpt-1, CCN1 may function as a chemoattractant for invading vascular/endothelial precursor cells that populate the glomerulus.

New visual clues were provided by serial MPM imaging of single JGA/GEnCs in the same Cdh5-Confetti mice (FIG. 15) suggesting that GEnCs can be clonally derived from resident EPCs localized at the terminal AA segment. Also, the Inventors observed rapid and robust remodeling of the glomerular endothelial layer that occurred within a few days, in response to both injury and CCN1. The above preliminary data indicate that CCN1 is a major regulator of GEnCs, and is involved in the embryonic development and maintenance of glomerular capillaries in the adult kidney.

In other preliminary experiments the Inventors tested the possibility that JGA-derived CCN1 may be released into the blood, and may act as a systemic angiogenic hormone. Blood was collected before and at different times after bilateral nephrectomy in both mice and rats as shown in FIG. 16. Plasma CCN1 levels continuously decayed after nephrectomy, suggesting that the kidney/JGA is a significant source of systemic CCN1 (FIG. 16A-B). Kidney, aorta, heart, and brain tissues were collected from two groups of inducible nNOS-CCN1 KO mice before and three weeks after tamoxifen induction, and sections stained for TUNEL assay of apoptosis. Compared to nearly undetectable levels in normal tissues before (not shown), a high number of vascular endothelial cells in all tissues stained TUNEL+ after JGA CCN1 deletion (FIG. 16C), indicating the presence of widespread systemic endothelial injury when renal CCN1 synthesis is compromised. These findings provide strong support the view that JGA-derived CCN1 is released into the blood and has vascular effects at distant organ sites.

It is very likely that in addition to well-established renal hormones (renin, erythropoietin) there are several other kidney-derived factors that act systemically, and their reduced levels cause systemic complications of CKD. For example, CKD patients have increased cardiovascular (CV) co-morbidities and mortality. Since CCN1 effects on endothelial cells is a key mechanism to maintain vascular integrity, JGA-derived CCN1 may be important in maintaining not only the renal vasculature, but systemic CV health as well. The Inventors' new data above suggest that reduced CCN1 levels in CKD may be involved in the development of CV complications.

Figure 17A:
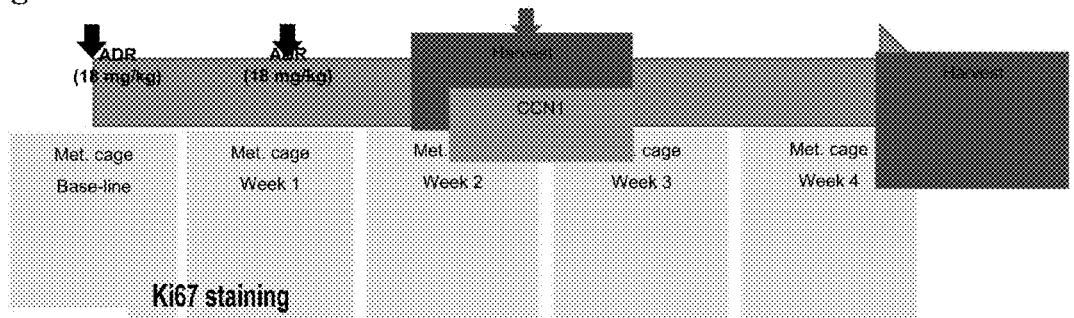
FIG. 17A: illustration of study design.
Figure 17B:
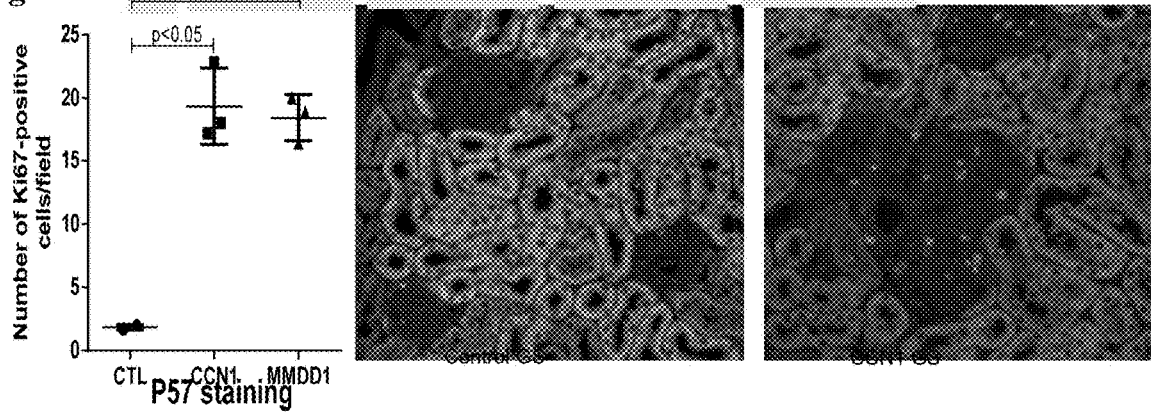
FIG. 17B: Effects of CCN1 and MMDD1 media on the number of Ki67+ cells (IF, red) per field.
Figure 17C:
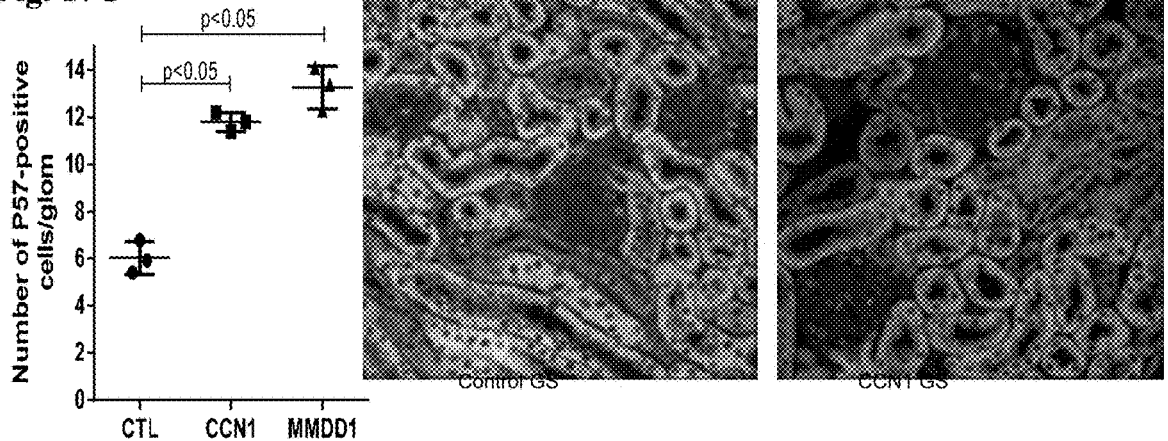
FIG. 17C: Effects of CCN1 and MMDD1 media on the number of p57+ podocytes (IF, red) per glomerulus. Green is autofluorescence for visualization of tissue anatomy.

In other preliminary experiments, mouse (ADR nephropathy resembling human-like FSGS) and rat (PAN-induced FSGS) models of CKD were established. Single renal subcapsular treatment with exogenous recombinant CCN1 was performed at a time point (two weeks after second ADR dose in mice, or after the second dose of PAN in rats) when severe and persistent glomerular pathology was confirmed (FIG. 17A), with subsequent two weeks' follow-up. Animals were placed in metabolic cages weekly for urine collection, and tissues (kidney, aorta, heart, brain, blood) harvested 4 weeks (after first ADR dose in mice), or 2 months (after first PAN dose in rats). FIG. 17B-C demonstrates that a single CCN1 treatment caused significant remodeling of sclerotic glomeruli indicated by the >20-fold increase in Ki67+ proliferating cells in glomeruli (FIG. 17B), and the significantly increased number of p57+ podocytes in the treated versus control groups (FIG. 17C).

These experiments support therapeutic approaches for glomerular diseases using CCN1 supplementation. Although renal subcapsular delivery works for the proposed pre-clinical animal models, the Inventors will further refine the exciting alternative approach of GEnC-targeted delivery of specific homing peptides. This would be an important step toward ultimately developing a clinically relevant non-invasive, iv injectable, specific glomerulus-targeting CCN therapy, to obviate the potential adverse effects of chronically very high plasma CCN1 (e.g. cancer). The robust angiogenesis, glomerular revascularization, podocyte preservation, and diminished proteinuria observed in preliminary mouse and rat studies of GS are extremely exciting, and suggest the major role of JGA, CCN1, and the glomerular endothelium in glomerular pathogenesis, and importantly, as an important novel therapeutic target. Reduced JGA CCN1 expression in CKD (FIG. 18) suggests the primary role of CCN1 in glomerular pathogenesis.

The translation of the pre-clinical animal data to the human kidney and CKD is of utmost importance and significance for the future development of clinical diagnostic and therapeutic approaches. Preliminary data indicated species differences in renal/JGA expression of CCN1 between rodents and human: CCN1 is expressed exclusively in MD cells in the human kidney, and not in JG renin cells.

Figure 18D:
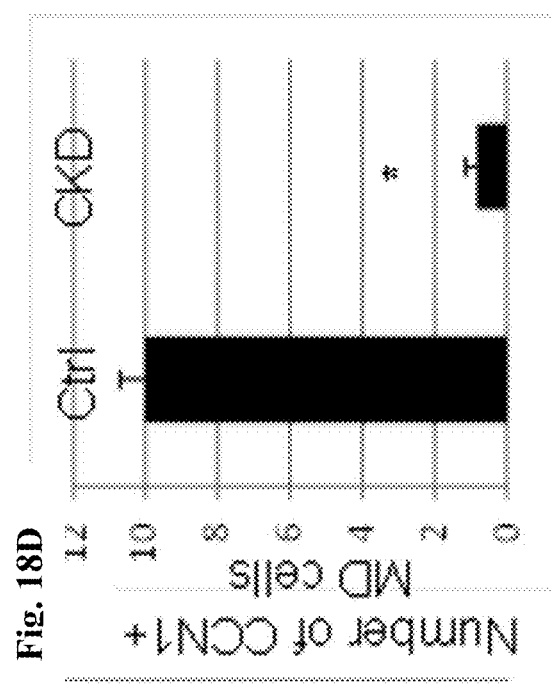

In preliminary experiments the Inventors aimed to study and translate this new nephron repair mechanism to the human kidney by using normal healthy and diseased human kidney tissues. Using IHC the Inventors found that CCN1 expression was 100% specific to cells of the MD in the human renal cortex and medulla (FIG. 18), and the number of CCN1+ MD cells was significantly reduced to almost undetectable levels in CKD patients (FIG. 18D).

Summary of the Therapeutic Approaches Used or being Developed:
1. Composition and method of using homing peptide plus miRNA
2. Composition and method of using the CCN1 peptide
3. Composition and method of using the conditioned MD cell culture media
4. Method of using small molecules, e.g. the loop diuretics Example 10

MD Homing Peptide Plus miRNA

In principle, the Inventors' therapeutic approach to activate and manipulate (switch-on/off) this new macula densa cell program of kidney tissue remodeling is the specific targeting of these cells and their specific genes by using specific MD binding peptide conjugated to specific miRNAs given iv injection.

In preliminary data, the Inventors identified a MMDD1 homing peptide based on phage-display, used it as targeting domain, and fused to a histidine-rich amphipathic peptide, optimized for DNA binding properties and gene delivery through endosomal escape. The fusiogenic peptide was synthesized:

NH2-ACFNDSDMLCGGGKKHLLAHALHLLALLALHLAHALAHLKKA[SEQ ID NO: 1]-NH2

Figure 19:
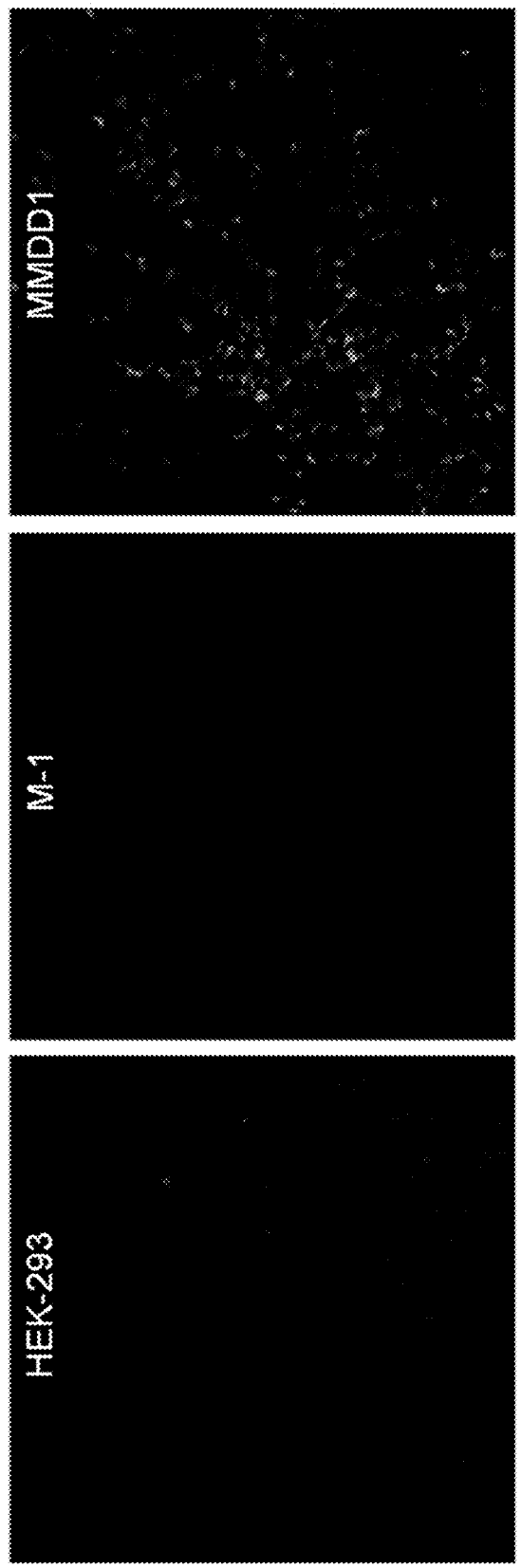
FIG. 19. Selective targeting of MD cells with the MMDD1 homing peptide. Incubation of various renal epithelial cell lines with a MD-specific fusion protein (MMDD1 homing peptide+GFP cDNA complex) resulted in successful transfection of MMDD1 cells with GFP, but not M-1 and HEK-293 cells. Note the diffuse cytosolic GFP expression in MMDD1 cells indicating successful escape of the endosomes after fusion protein internalization.

The peptide was mixed with pcDNA3.1 GFP and incubated for 1 hour at room temperature. The solution was added to cultured MMDD1 cells (MD cell line), HEK293 cells and M-1 cells (collecting duct cell line), and incubated overnight at 37° C. in a humidified atmosphere (95% air and 5% CO2). Transfection was measured by fluorescence microscopy. FIG. 19 demonstrates that this MD-specific targeting and gene delivery approach is working.

Figure 20:
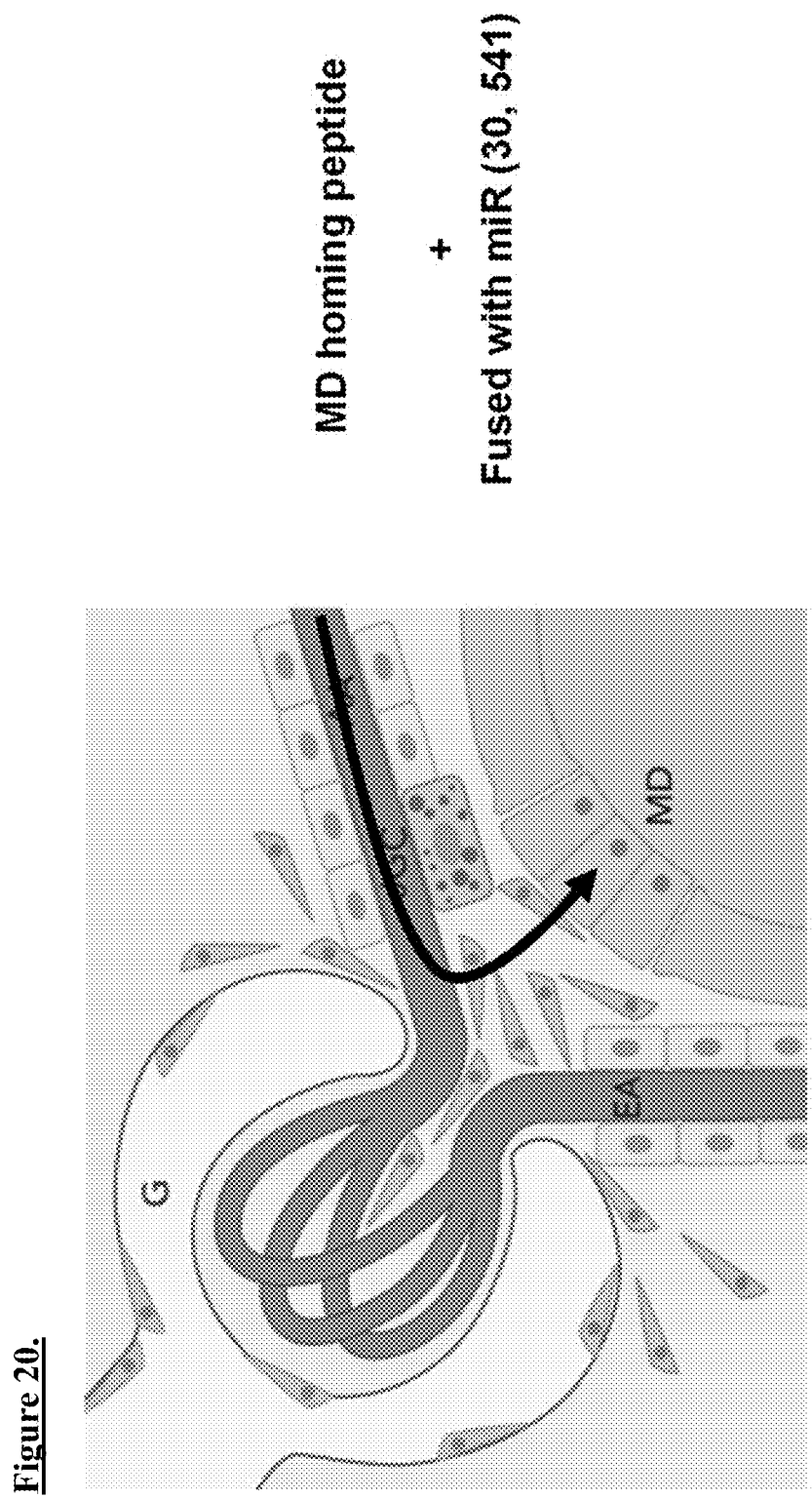
FIG. 20. Schematic of the Inventors' biologics-based specific MD cell targeting approach for developing new therapeutics for CKD.

In addition, the Inventors are currently working to fine-tune the MD binding peptide, and to identify the specific regulatory miRNA that is specific for MD cells and is enriched in MD cells under the low salt+ACEI activated condition. Deep sequencing and miRNA sequencing approaches are currently ongoing (as illustrated in FIG. 8D) to identify the specific MD miRNA that is responsible for turning on transcription factors in MD cells that in turn activate the set of gene families involved in the MD nephron repair program (FIG. 8-9). Top candidates currently are miR-30 and miR-541. When identified, the MD homing peptide will be conjugated to the regulatory miRNA and the entire complex injected iv. This is a classic biologics approach using specific and biologically relevant peptides and regulatory RNAs to specifically target and amplify the MD kidney tissue repair program (FIG. 20).

Various candidate miRNAs can include those expressed by MD cells under the stimulated (low salt diet+ACE inhibitors) condition. The Inventors continue to identify the exact miRNA types involved (by performing miRNA sequencing). Once identified, one delivers these regulatory miRNAs into MD cells using MD homing peptides, or in case the miRNA is very specific for MD cells, by simply injecting it iv. By delivering the specific miRNAs, one can "mimic" the activated state of MD cells under which they endogenously turn on this remodeling program. And of course by the proper dosing of miRNAs to amplify the level of activity.

Without being bound by any theory, it is suggested that these miRNAs regulate the expression of key developmental transcription factors Bmp and Wnt (Bmp3/7 and Wnt10a to be precise in MD cells). By turing on these transcription factors, these will in turn activate the entire MD repair program, and the many different gene families involved, including secreted angiogenic peptides (CCN1, Pappa-2, Gdf15, FGF2, etc), extracellular matrix remodeling enzymes (MMP14, tissue kallikreins, etc), patterning factors (robo, slit), growth factors and their receptors (NGF, FGF2, etc). In this regard, the Inventors think it will be important to develop not only "on" switches, but also "off" switches that can turn off this genetic program. The Inventors have evidence that sustained prolonged overactivity of this otherwise protective mechanism can also lead to pathology. As seen in other models and diseases, the balance is what really matters. Too little of a good thing is bad, but too much of a good thing is also bad.

One would seek to avoid extreme neovascularization of kidney tissue (as potentially tumorigenic), or tissue fibrosis or sclerosis. It is possible that certain naturally occurring miRNAs will have a certain limited lifetime, so one may not have to worry about their sustained activity. But preventing over-activation is also potentially therapeutic, and therefore of interest would be to develop tools for "off" switches. In diabetes for example, kidney pathology is caused by sustained overactivation of this MD-driven kidney tissue remodeling program, causing fibroblast invasion, mesangial expansion, glomerular neovascularization, and ultimately segmental glomerulosclerosis and tubulo-interstitial fibrosis. In the case of diabetic nephropathy (in contrast to most other primary kidney diseases in which the Inventors need to activate), the therapeutic approach would be the blockade of the MD hyperactivity. By administering inhibitory miRNAs of the same tissue remodeling program. One can identify these the same way one identifies stimulatory miRNAs, simply by performing miRNA collection, isolation, and sequencing under the inhibitory condition, which is high salt diet. The top enriched, and MD-specific miRNAs under the high salt condition will give us the endogenous miRNA type(s) that the Inventors will need to deliver, by the same MD homing peptide-mediated targeting approach.

Example 11

CCN1 Peptide

Since the main problem in kidney disease appears to be reduced or absent production of CCN1 by macula densa cells, the Inventors can supplement recombinant CCN1 peptide delivered specifically into the renal parenchyma. In preliminary studies illustrated in FIG. 17, the Inventors used subcapsular injections of recombinant CCN1. However, this is invasive procedure, which would have limited clinical use. A much better non-invasive approach the Inventors are currently testing is to give systemic iv injection of recombinant CCN1 targeted specifically to the kidney blood supply. This is performed by conjugating recombinant CCN1 to a glomerulus homing peptide. The promise and therapeutic benefit of this approach is shown in FIG. 17 in a pre-clinical animal model of CKD.

Example 12

Conditioned MD Cell Culture Media

Figure 21:
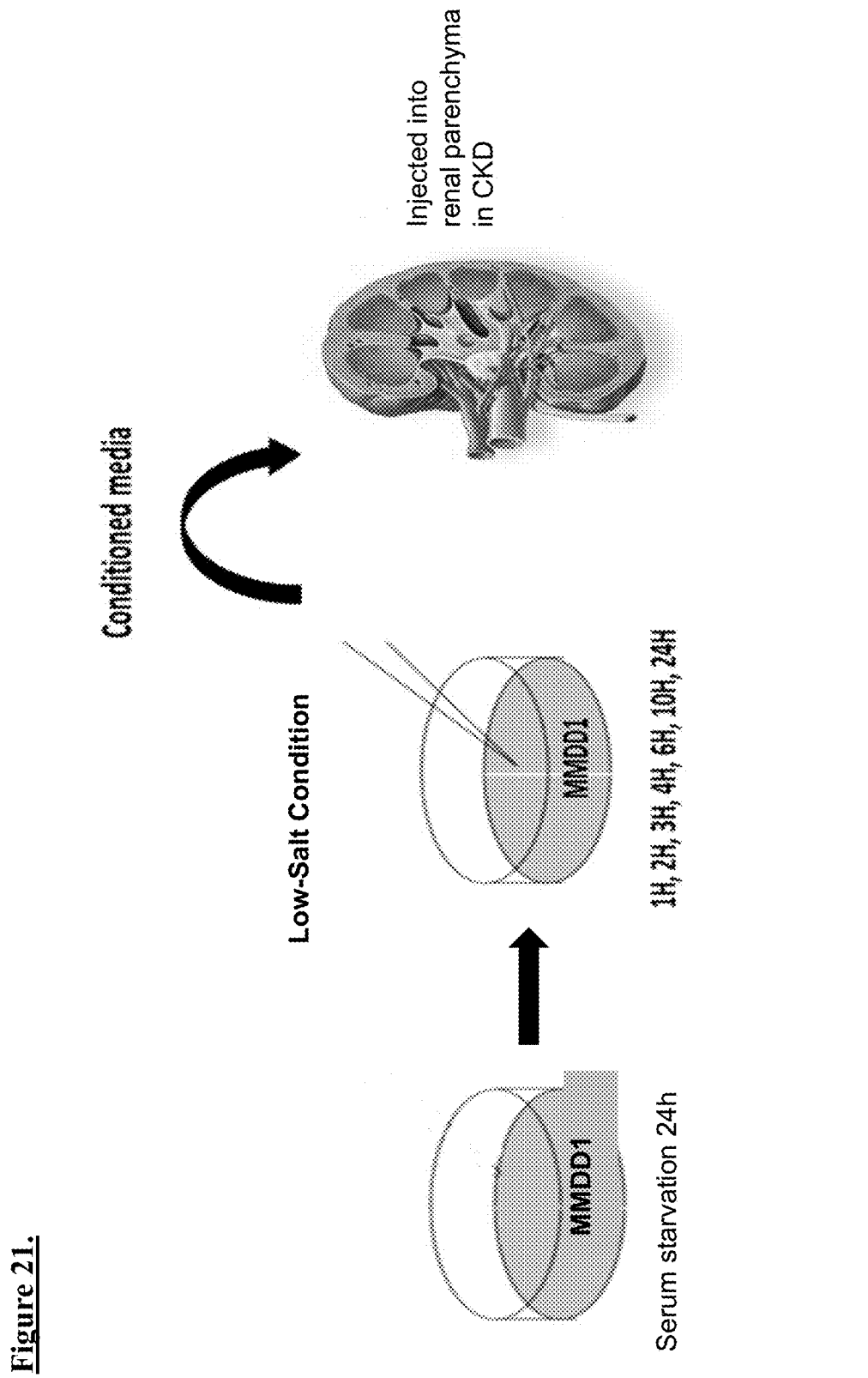
FIG. 21. Schematic illustration of the Inventors' new therapeutic strategy using conditioned MD cell culture media.

The Inventors discovered and convincingly demonstrated the novel tissue remodeling role of MD cells in vivo, which is mediated by a variety of MD cell-specific secreted angiogenic peptides and progenitor cell homing paracrine mediators including PGE2, NO, Ccn1, Fgf2, Gdf15, Pappa-2 (FIGS. 6-9, 18). In order to reproduce all of these MD-specific protective factors for therapeutic use, the Inventors utilized the existing MMDD1 in vitro cell culture model of MD cells that endogenously produce these factors. Mimicking the in vivo physiological activation of MD cells (low salt diet), the NaCl content of MD tissue culture medium was reduced by half as described earlier. The incubation of MMDD1 cells with low salt culture media for longer than 3 hours resulted in the endogenous production of angiogenic and glomerulotrophic MD factors in high amounts. The treatment of cultured GEnCs with this conditioned MMDD1 culture media resulted in robust tube formation, endothelial cell migration and proliferation (similar to as shown in FIG. 11). Importantly, the injection of conditioned MMDD1 media into the renal parenchyma of CKD animals resulted in significant structural improvement (FIG. 17). The therapeutic strategy with this medium (illustrated in FIG. 21) is the same as above for CCN1, to inject it under the renal capsule for specific kidney targeting.

Example 13

Small Molecules

Figure 22:
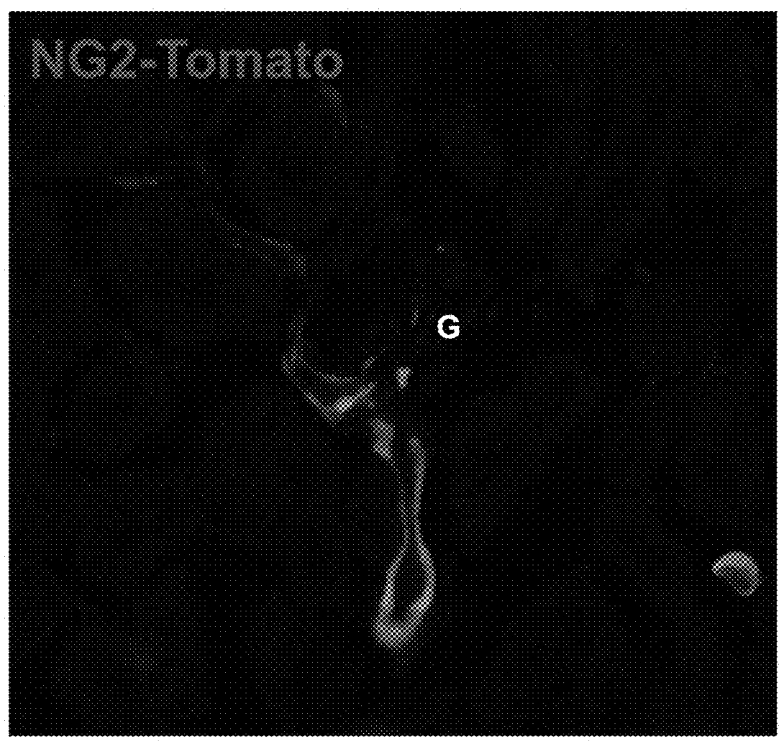
FIG. 22. Robust vascular and glomerular remodeling in response to 10 days of furosemide treatment. Increase in renal cortical mesenchyme-derived cell density (red), remodeling of the entire length of the glomerular (G) arterioles by NG2-derived progenitor cells within 10 days in response to loop diuretics.

The Inventors' initial experimental strategy to show proof-of-principle for this macula densa mechanism was to apply gold-standard whole body approaches to activate this new mechanism (e.g. dietary salt restriction and loop diuretics), which have been known for decades to improve kidney function. One example is the use of the loop diuretic furosemide, which blocks salt-sensing by MD cells and therefore is equivalent to the effects of low dietary salt intake as shown in FIGS. 6-7, 10). In fact, the application of furosemide for 10 days in an animal model resulted in significant kidney tissue remodeling (FIG. 22), similarly to the use of dietary salt restriction and ACEI treatment (FIG. 10). Furosemide and other loop diuretics have been in human clinical use for decades as efficient anti-hypertensive therapies. In addition to diuretics, the Inventors will explore other small molecules that may have specific MD cell targeting characteristics, and may activate the MD kidney repair program.

Example 14

Bona Fide MD Cells

The Inventors developed new, 100% specific mouse and human macula densa (MD) cell primary cultures and immortalized MD cell lines. The current leading MD cell line, the MMDD1 cell culture, is generally known to possess only a subset of MD cell properties (i.e., MD cell-like) and not entirely resembling true MD cell features. Bona fide MD cells will aid in development of in vitro research tools that allow high throughput future investigation of macula densa cell biology, molecular expression and secretion, and cell function, etc. The establishment of both mouse and human MD cells helps the translation of the Inventors' pre-clinical results to the human condition. Further, new and specific MD cell cultures that mirror in vivo regenerative cell functions serve the foundation of, and can be further developed into cell-based biological therapeutic strategies for CKD.

The successful establishment and features of new mouse and human macula densa primary cell cultures and immortalized cell lines (mMD and hMD cells) that the Inventors developed are shown in FIG. 23. Mouse macula densa (mMD) cells were derived from nNOS-mTmG mouse kidneys, taking advantage of the 100% MD cell-specific GFP expression in the cortex of these kidneys. After quick tissue digestion of freshly harvested mouse kidneys, dispersed renal cortical cells were FACS sorted, and MD cells isolated based on their green fluorescence (due to mGFP expression). Fluorescence microscopy of these freshly isolated MD cells identified specific and unique MD cell features, such as the presence and high density of long basal nanotubes (FIG. 23A). Physiological studies revealed that the density of these MD nanotubes is regulated, showing significant increases in females versus males (gender specificity) and in response to the condition of body fluid and salt loss (induced by dietary salt restriction and ACE inhibitor treatment for two weeks). Transmission electron microscopy of the mouse, rat, rabbit, and human kidneys showed that these MD nanotubes arborize and invade the entire extraglomerular mesangium, form close contacts with the vessel wall of glomerular arterioles, and contain numerous electron-dense vesicles (not shown). Immunofluorescence studies confirmed that CCN1 is part of the vesicle cargo in MD cells and in their nanotubes (FIG. 23E). These results strongly suggest the presence of detailed cell-to-cell paracrine communication network between MD cells and various vascular and mesangial cell types, and that MD cells have the capacity and machinery to focally deliver angiogenic and tissue remodeling factors to nearby target cells.

Figure 23A:
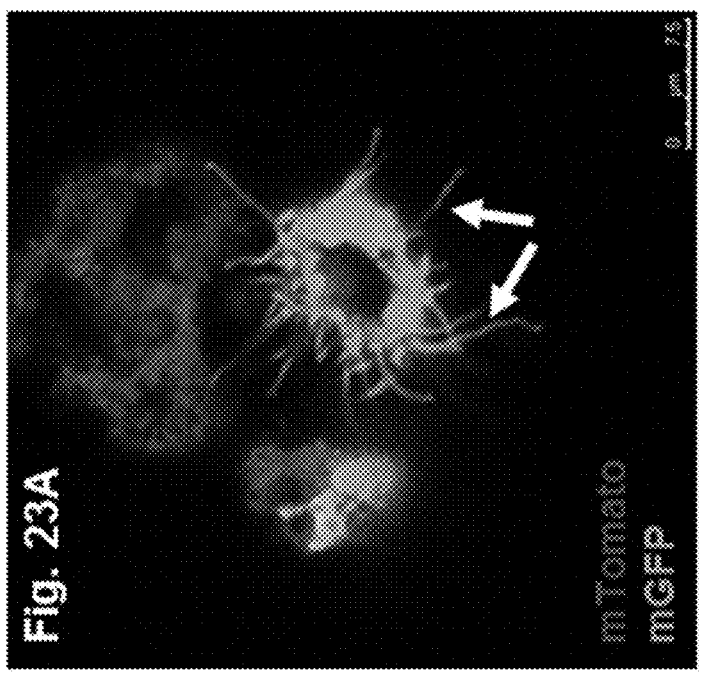
FIG. 23A: Freshly FACS sorted, nNOS-mTmG mouse kidney-derived mouse macula densa (mMD) cells (green due to mGFP) are shown with attached adjacent distal tubule and extraglomerular mesangial cells (red, due to mTomato). Arrows point at the unique feature of mMD cells, the presence and high density of long basolateral nanotubes.
Figure 23B:
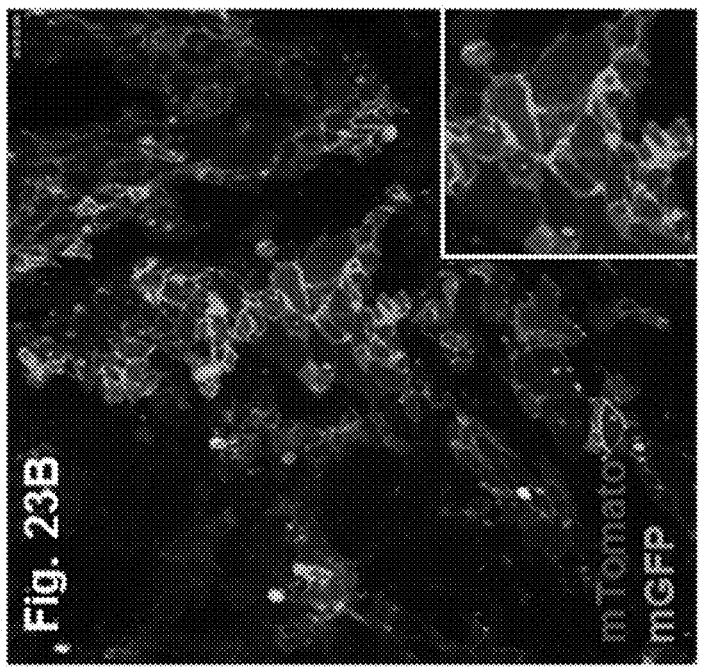
FIG. 23B: Fluorescence image of a mixed cell culture with high density of mMD cells (green) after immortalization. Inset shows a magnified region with typical features of high membrane-targeted GFP fluorescence with confluent epithelia-specific cobblestone pattern.
Figure 23E:
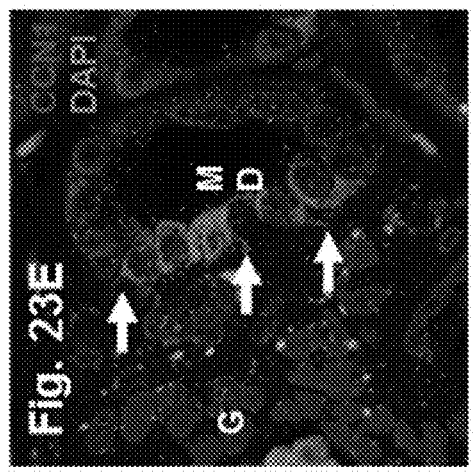
FIG. 23E: Ccn1 immunofluorescence (red) of human kidney section showing macula densa cell-specific labeling with a vesicular pattern that is extended into long basal cell processes (arrows) that invade the extraglomerular mesangium. Cell nuclei are labeled with DAPI (blue). G: glomerulus.
Figure 23D:
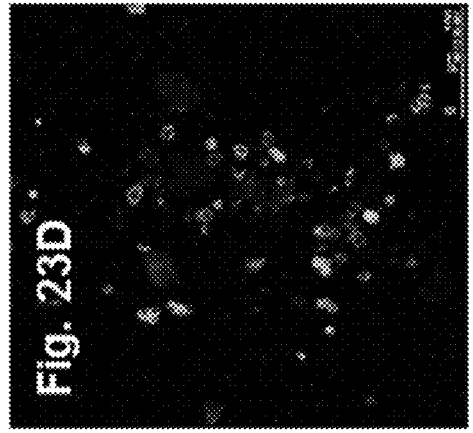
FIG. 23D: Due to self-aggregation, dense plaques of freshly sorted macula densa cells (green) develop within 15 min.
Figure 23C:
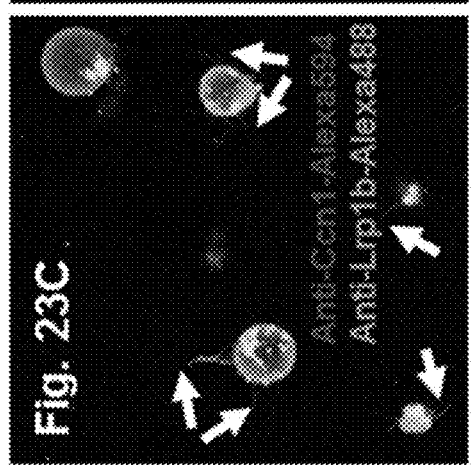
FIG. 23C: Freshly sorted human macula densa (hMD) cells showing cell surface labeling due to Lrp1b antibody binding (green), and intracellular vesicular labeling due to Ccn1 antibody uptake (red). Long nanotubes and primary cilia are indicated by arrows.

Similarly to mouse MD cells, human macula densa (hMD) cells were successfully isolated and cultured using fresh nephrectomy samples from local human surgeries with approved IRB protocols. Human MD cells were FACS sorted from freshly obtained and quickly digested human kidney tissues, based on MD cell-specific surface labeling with anti-Lrp1b (green), and intracellular vesicular labeling with anti-Ccn1 (red) antibodies. Human MD cells also feature numerous, long basal nanotubes (FIG. 23C), and highly dynamic pseudopod formation (motility) that causes spontaneous self-aggregation of freshly isolated MD cells, resulting in the formation of several multi-cell MD plaques within 15 min (FIG. 23D). The successful immortalization and features of newly established MD cell cultures are shown in FIG. 23B. MD cell immortalization was performed by using commercially available common tools and procedures, including lentiviral vectors for the transfection of MD primary cell cultures with the SV40 T antigen (tsA58 temperature sensitive mutant, Abm, Vancouver, Canada). In this system, rapid growth of MD cells is achieved by culturing at 33 degrees Celsius, while MD cells differentiate at 37 degrees Celsius.

Example 15

Disease Modeling and Therapeutic Studies Using Bona Fide MD Cells

Figure 24A:
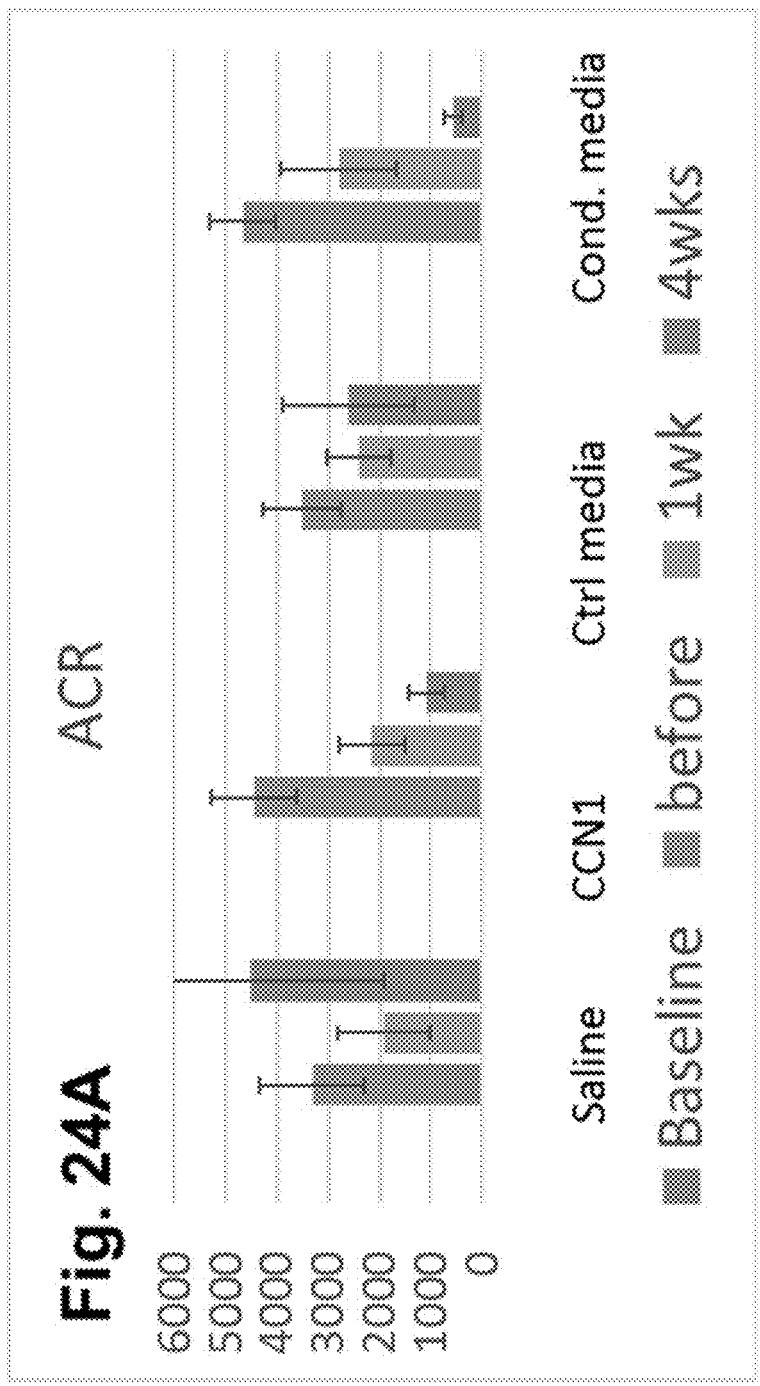
FIG. 24A: Albuminuria (albumin/creatinine ratio, ACR) in the various control and treatment groups before ADR-induced kidney injury (baseline), two weeks later before the start of treatments, and 1 and 4 weeks after treatment with saline, recombinant CCN1, control or low salt-conditioned MD cell media.
Figure 24C:
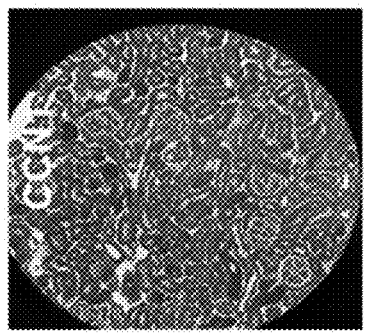
FIG. 24B-FIG. 24C: Trichrome staining of kidney histological sections. Robust glomerulosclerosis and tissue fibrosis (indicated by amount of blue color) in control saline-treated (FIG. 24B), and improved pathology (lack of blue) in the CCN1-treated experimental group.
Figure 24B:
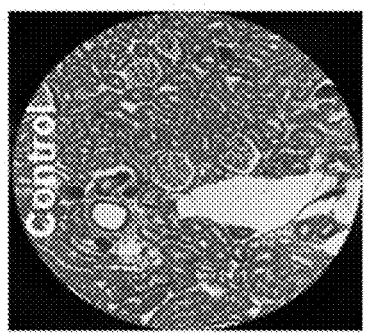

In other work The Inventors tested the effects and therapeutic potential of the aforementioned novel biologicals. The robust protective effects of treatment with recombinant CCN1 or conditioned MD cell media in the BalbC Adriamycin mouse model of human-like focal segmental glomerulosclerosis (FSGS) in vivo is shown in FIG. 24. In these experiments, the Inventors intentionally generated a robust, pre-existing pathological condition, before starting new therapeutic treatment regimens. Rather than a prevention approach, the Inventors' strategy is consistent with the human clinical problem, that patients need new therapies that cause regression of existing kidney disease. The development of albuminuria, the most important and clinically relevant functional readout of the failing kidneys was measured in the various control and experimental treatment groups before ADR-induced kidney injury (baseline), two weeks later before the start of treatments, and 1 and 4 weeks after treatment with saline, recombinant CCN1, control or low salt-conditioned MD cell media. FIG. 24A shows that 8 mg/kg ADR injection iv induced robust kidney pathology, based on high levels of albuminuria (FIG. 24A) and significant renal tissue fibrosis (FIG. 24B). Importantly, both CCN1 (3 mg injected iv once per day for 5 consecutive days) and conditioned MD medium treatment (200 ul ip injections for 5 consecutive days) caused a robust decline in albuminuria (FIG. 24A), indicating significant improvements in kidney function. Saline-treated or control, un-conditioned MD cell media did not have these effects (FIG. 24A). Subsequent kidney histological analysis showed robust glomerulosclerosis and tissue fibrosis in control saline-treated, and improved pathology in the CCN1-treated experimental group (FIG. 24B-C).

Figure 25:
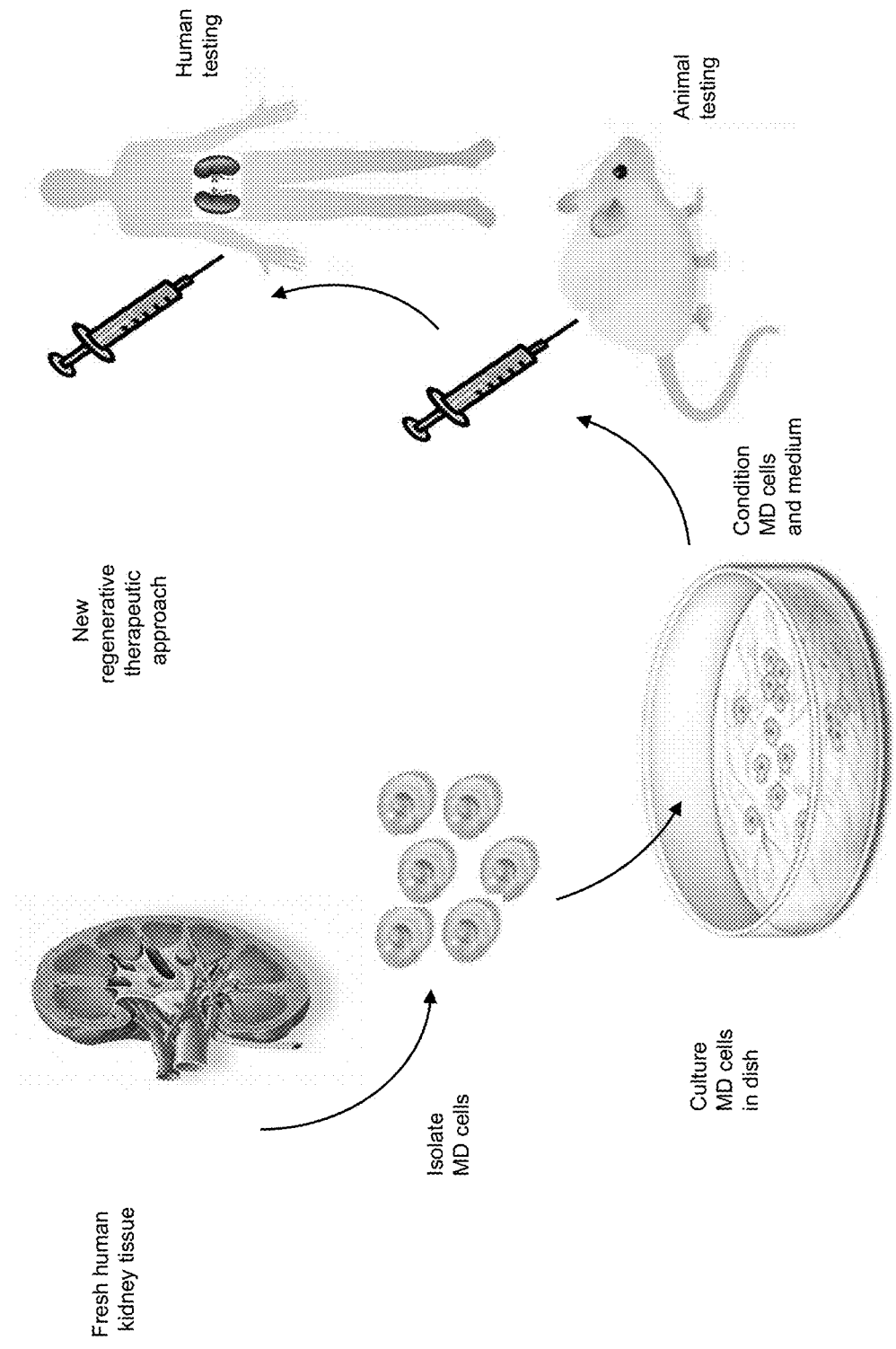
FIG. 25. Schematic drawing of the Inventors' therapeutic approaches to develop various MD cell-based biologicals as new therapy for human CKD. These include primary and immortalized MD cells, conditioned MD cell culture media, a combination of MD cell-specific molecular factors (CCN1, regulatory miRNAs) produced endogenously by newly established cultured MD cells.

FIG. 25 summarizes and illustrates the Inventors' novel therapeutic approaches to develop various MD cell-based biologicals as new therapy for human CKD. These include primary and immortalized MD cells, conditioned MD cell culture media, a combination of MD cell-specific molecular factors (CCN1, regulatory miRNAs) that are produced endogenously by newly established MD cell cultures.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are methods and compositions related to promoting proliferation, mobilization, migration of macula densa (MD) cells, diagnostic, prognostic and therapeutic techniques related to manipulation of MD cells or biomarker detection of MD cells, as related to kidney disease, and the particular use of the products created through the teachings of the invention.

Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

---

---

The invention claimed is:

1. A composition comprising media that was used to culture human macula densa (md) cells and comprising a protein secreted into the media by the human md cells.

2. A method of treating chronic kidney disease comprising administering the composition of claim 1 to a subject in need thereof.

3. The composition of claim 1, wherein the human md cells are primary cells.

4. The composition of claim 1, wherein the human md cells are immortalized.

5. The composition of claim 1, wherein the media is prepared by a method comprising starving the human md cells for about 24 hours; and culturing the human md cells in the media for at least three hours.

6. The composition of claim 5, wherein the media is a low salt media.

7. The composition of claim 1, wherein the media is enriched in angiogenic factors, or glomerulotropic factor, or both.

8. The method of claim 2, wherein the method of treatment comprises:
administering the composition by injection under the renal capsule.

9. The composition of claim 1, wherein the secreted protein is one or more of CCN family member 1 (CCN1), Pregnancy-associated plasma protein A2 (Pappa-2), nephroblastoma overexpressed (Nov), Vascular endothelial growth factor (VEGF), Bone morphogenetic protein 3 (BMP3), Matrix Metallopeptidase 14 (MMP14), or Growth/differentiation factor 15 (GDF15).

10. The composition of claim 1, wherein the media further comprises a growth factor.

11. The composition of claim 10, wherein the growth factor is Nerve growth factor (NGF) or Fibroblast Growth Factor 2 (FGF2).

12. The composition of claim 11, wherein the secreted protein is one or more of CCN family member 1 (CCN1), Pregnancy-associated plasma protein A2 (Pappa-2), nephroblastoma overexpressed (Nov), Vascular endothelial growth factor (VEGF), Bone morphogenetic protein 3 (BMP3), Matrix Metallopeptidase 14 (MMP14), or Growth/differentiation factor 15 (GDF15).

* * * * *